US010842777B2

(12) United States Patent
Graef et al.

(10) Patent No.: US 10,842,777 B2
(45) Date of Patent: *Nov. 24, 2020

(54) COMPOUNDS AND COMPOSITIONS THAT BIND AND STABILIZE TRANSTHYRETIN AND THEIR USE FOR INHIBITING TRANSTHYRETIN AMYLOIDOSIS AND PROTEIN-PROTEIN INTERACTIONS

(71) Applicant: The Board of Trustees of the Leland Stanford Junior University, Stanford, CA (US)

(72) Inventors: Isabella A. Graef, Woodside, CA (US); Mamoun M. Alhamadsheh, Fremont, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/510,574

(22) Filed: Jul. 12, 2019

(65) Prior Publication Data

US 2020/0093797 A1 Mar. 26, 2020

Related U.S. Application Data

(63) Continuation of application No. 15/883,750, filed on Jan. 30, 2018, now Pat. No. 10,398,681, which is a continuation of application No. 15/480,139, filed on Apr. 5, 2017, now Pat. No. 9,913,826, which is a continuation of application No. 14/876,447, filed on Oct. 6, 2015, now Pat. No. 9,642,838, which is a continuation of application No. 13/830,731, filed on Mar. 14, 2013, now Pat. No. 9,169,214.

(60) Provisional application No. 61/745,089, filed on Dec. 21, 2012.

(51) Int. Cl.
*A61K 31/415* (2006.01)
*C07D 231/12* (2006.01)
*C07D 237/08* (2006.01)

(52) U.S. Cl.
CPC .......... *A61K 31/415* (2013.01); *C07D 231/12* (2013.01); *C07D 237/08* (2013.01)

(58) Field of Classification Search
None
See application file for complete search history.

(56) References Cited

U.S. PATENT DOCUMENTS

| | | | |
|---|---|---|---|
| RE28,819 E | 5/1976 | Thompson | |
| 4,232,161 A | 11/1980 | Diana et al. | |
| 4,234,725 A | 11/1980 | Diana et al. | |
| 4,261,928 A | 4/1981 | Diana et al. | |
| 4,328,245 A | 5/1982 | Yu et al. | |
| 4,358,603 A | 11/1982 | Yu | |
| 4,409,239 A | 10/1983 | Yu | |
| 4,410,545 A | 10/1983 | Yu et al. | |
| 4,522,811 A | 6/1985 | Eppstein et al. | |
| 5,709,874 A | 1/1998 | Hanson et al. | |
| 5,759,542 A | 6/1998 | Gurewich | |
| 5,840,674 A | 11/1998 | Yatvin et al. | |
| 5,860,957 A | 1/1999 | Jacobsen et al. | |
| 5,900,252 A | 5/1999 | Calanchi et al. | |
| 5,948,433 A | 9/1999 | Burton et al. | |
| 5,972,366 A | 10/1999 | Haynes et al. | |
| 5,983,134 A | 11/1999 | Ostrow | |
| 5,985,307 A | 11/1999 | Hanson et al. | |
| 5,985,317 A | 11/1999 | Venkateshwaran et al. | |
| 6,004,534 A | 12/1999 | Langer et al. | |
| 6,010,715 A | 1/2000 | Wick et al. | |
| 6,024,975 A | 2/2000 | D'Angelo et al. | |
| 6,039,975 A | 3/2000 | Shah et al. | |
| 6,048,736 A | 4/2000 | Kosak | |
| 6,060,082 A | 5/2000 | Chen et al. | |
| 6,071,495 A | 6/2000 | Unger et al. | |
| 6,120,751 A | 9/2000 | Unger | |
| 6,131,570 A | 10/2000 | Schuster et al. | |
| 6,139,865 A | 10/2000 | Friend et al. | |
| 6,167,301 A | 12/2000 | Flower et al. | |
| 6,253,872 B1 | 7/2001 | Neumann | |
| 6,256,533 B1 | 7/2001 | Yuzhakov et al. | |
| 6,261,595 B1 | 7/2001 | Stanley et al. | |
| 6,267,983 B1 | 7/2001 | Fujii et al. | |

(Continued)

FOREIGN PATENT DOCUMENTS

| | | |
|---|---|---|
| DE | 2834322 | 2/1979 |
| EP | 1445249 | 8/2004 |

(Continued)

OTHER PUBLICATIONS

Alhamadsheh et al., "Potent Kinetic Stabilizers that Prevent Transthyretin-mediated Cardiomyocyte Proteotoxicity," Science Translational Medicine 3(97):1-9 (2011).
Arkin et al., "Small-molecule inhibitors of protein—protein interactions: progressing towards the dream," Nat Rev Drug Discov 3(4):301-317 (2004).
Buxbaum et al., "Significance of the amyloidogenic transthyretin Val 122 Ile allele in African Americans in the Arteriosclerosis Risk in Communities (ARIC) and Cardiovascular Health (CHS) Studies," Am Heart J 159:864-870 (2010).
Choi et al., "Antidiabetic actions of a non-agonist PPARγ ligand blocking Cdk5-mediated phosphorylation," Nature 477(7365):477-481 (2011).

(Continued)

*Primary Examiner* — Kamal A Saeed
(74) *Attorney, Agent, or Firm* — Edward J. Baba; Bozicevic, Field & Francis LLP

(57) ABSTRACT

Disclosed herein are compounds and compositions thereof which find use in increasing stability of proteins particularly proteins that tend to misfold and form aggregates. Also provided herein are methods for using these compounds and compositions for increasing stability of proteins and thereby decreasing aggregate formation by these proteins. Also disclosed herein are heterobifunctional compounds that include a TTR binding compound connected to a targeting moiety via a linker, for use in disrupting PPIs of a target protein.

9 Claims, 7 Drawing Sheets

(56) References Cited

U.S. PATENT DOCUMENTS

| | | |
|---|---|---|
| 6,271,359 B1 | 9/2001 | Norris et al. |
| 6,274,552 B1 | 9/2001 | Tamarkin et al. |
| 6,316,652 B1 | 11/2001 | Steliou |
| 7,214,695 B2 | 5/2007 | Kelly et al. |
| 8,877,795 B2 | 11/2014 | Graef et al. |
| 9,913,826 B2 | 3/2018 | Graef et al. |
| 2008/0319077 A1 | 12/2008 | Nobuhiro |
| 2010/0249094 A1 | 9/2010 | Kap-Sun |

FOREIGN PATENT DOCUMENTS

| | | |
|---|---|---|
| SU | 1824398 | 1/1993 |
| WO | WO95/12815 | 5/1995 |
| WO | WO98/27972 | 7/1998 |
| WO | WO00/59874 | 10/2000 |
| WO | WO02/059621 | 1/2002 |
| WO | WO02/088101 | 11/2002 |
| WO | WO03/099793 | 12/2003 |
| WO | WO2004/056315 | 7/2004 |
| WO | WO2004/063166 | 7/2004 |
| WO | WO2008/016811 | 2/2008 |
| WO | WO2008/145616 | 12/2008 |
| WO | WO2009/148961 | 12/2009 |
| WO | WO2010/010190 | 1/2010 |
| WO | WO2010/030592 | 3/2010 |
| WO | WO2010/059658 | 5/2010 |
| WO | WO2011/046771 | 4/2011 |
| WO | WO2011/053948 | 5/2011 |
| WO | WO2011/140333 | 11/2011 |
| WO | WO2012/082566 | 6/2012 |

OTHER PUBLICATIONS

Coelho, "Familial amyloid polyneuropathy: new developments in genetics and treatment," Current opinion in neurology 9(5):355-359 (1996).

Connelly et al., "Structure-based design of kinetic stabilizers that ameliorate the transthyretin amyloidosis," Curr Opin Struct Biol 20:54-62 (2010).

Connors et al., "Cardiac amyloidosis in African Americans: Comparison of clinical and laboratory features of transthyretin V122I amyloidosis and immunoglobulin light chain amyloidosis," Am Heart J 158(4):607-614 (2009).

Diana et al., "Synthesis and antiherpetic activity of some 4-[(aryloxy)alkyl]pyrazoles," Journal of Medicinal Chemistry 24(6):731-735 (1981).

Falk et al., "The Systemic Amyloidoses," N Eng J Med 337:898-909 (1997).

Gell et al., "The Detection and Quantitation of Protein Oligomerization,"Adv Exp Med Biol 747:19-41 (2012).

Haigis et al., "The Aging Stress Response," Mol Cell 40(2):333-344 (2010).

Jacobson et al., "Variant-Sequence Transthyretin (Isoleucine 122) in Late-Onset Cardiac Amyloidosis in Black Americans," N Engl J Med 336:466-473 (1997).

Jiang et al., "The V122I cardiomyopathy variant of transthyretin increases the velocity of rate-limiting tetramer dissociation, resulting in accelerated amyloidosis," Proc Natl Acad Sci USA 98(26):14943-14948 (2001).

Joao and Saraiva, "Transthyretin mutations in health and disease," Hum Mutat 5:191-196 (1995).

Katritzky et al., "Mannich reactions of carbonyl compounds and enamines with benzotriazole as the NH component," Journal of Heterocyclic Chemistry 31(4):917-923 (1994).

Miyawaki, "Development of Probes for Cellular Functions Using Fluorescent Proteins and Fluorescence Resonance Energy Transfer," Annu Rev Biochem 7(80):357-373 (2011).

Ouyang et al., "Syntheses of 4-(2-Hydroperoxy-2,2-diarylethyl)-3,5-dimethylpyrazoles, 4-(2-Hydroxy-2,2-diarylethyl)-3,5-dimethylpyrazoles, and the Related Compounds," Journal of Heterocyclic Chemistry 33(4):1291-1302 (1996).

Ran et al., "Non-Conjugated Small Molecule FRET for Differentiating Monomers from Higher Molecular Weight Amyloid Beta Species," PLoS ONE 6(4):e19362:1-6 (2011).

Reixach et al., "Tissue damage in the amyloidosis: Transthyretin monomers and nonnative oligomers are the major cytotoxic species in tissue culture," Proc Natl Acad Sci USA 101:2817-2822 (2004).

Saraiva et al., "Transthyretin mutations in hyperthyroxinemia and amyloid diseases," Hum Mut 17(6):493-503 (2001).

Saraiva et al., "Transthyretin mutations in health and disease," Hum Mutat 5:191-196 (1995).

Selkoe et al., "Cell Biology of protein misfolding: The examples of Alzheimer's and Parlinson's diseases," Nat Cell Biol 6:1054-1061 (2004).

Selkoe et al., "Folding proteins in fatal ways," Nature 426:900-904 (2003).

Stefani et. al., "Protein misfolding and aggregation: new examples in medicine and biology of the dark side of the protein world," Biochimica et biophysica acta 1739:5-25 (2004).

Wojtczak et al., "Structures of Human Transthyretin Complexed with Thyrixine at 2.0 A Resolution and 3', 5'-Dinitro-N-aceytyl-L-thyronine at 2,2 A Resolution," Acta Cryst D52:758-765 (1996).

Zefirov et al., "Ring-Opening Reactions of 1,1-diacetylcyclopropane with Hydrazine and Hydroxylamine Derivatives as the Novel Synthesis of β-X-ethyl Substituted Pyrazoles and Isoxazoles," Tetrahedron 38(11):1693-1697 (1982).

Figure 4
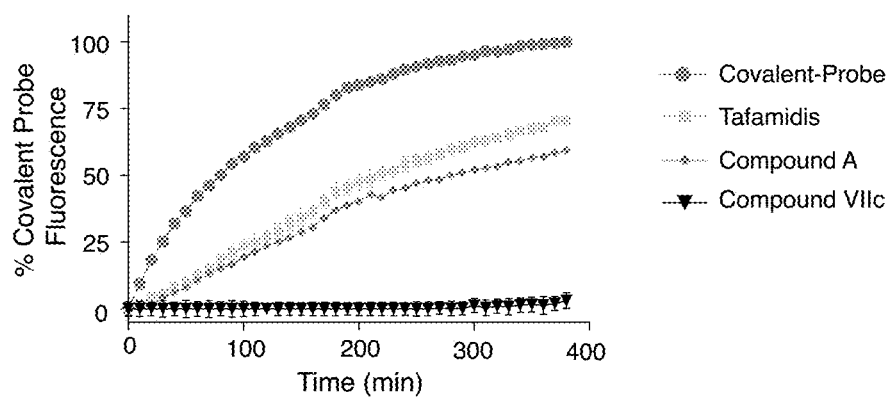
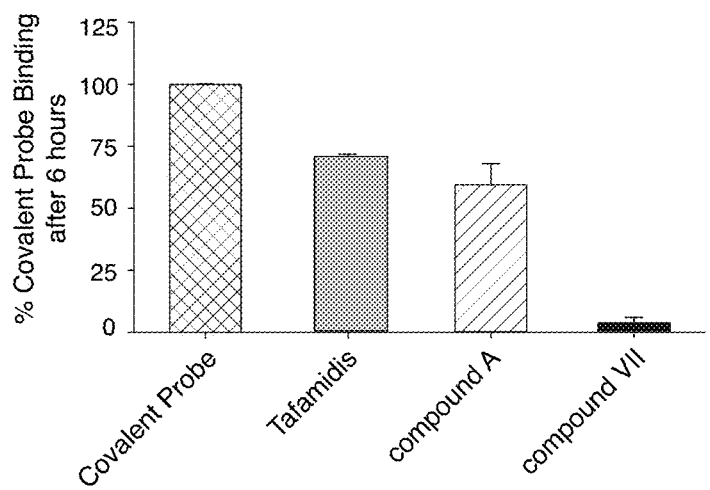

Figure 5
A
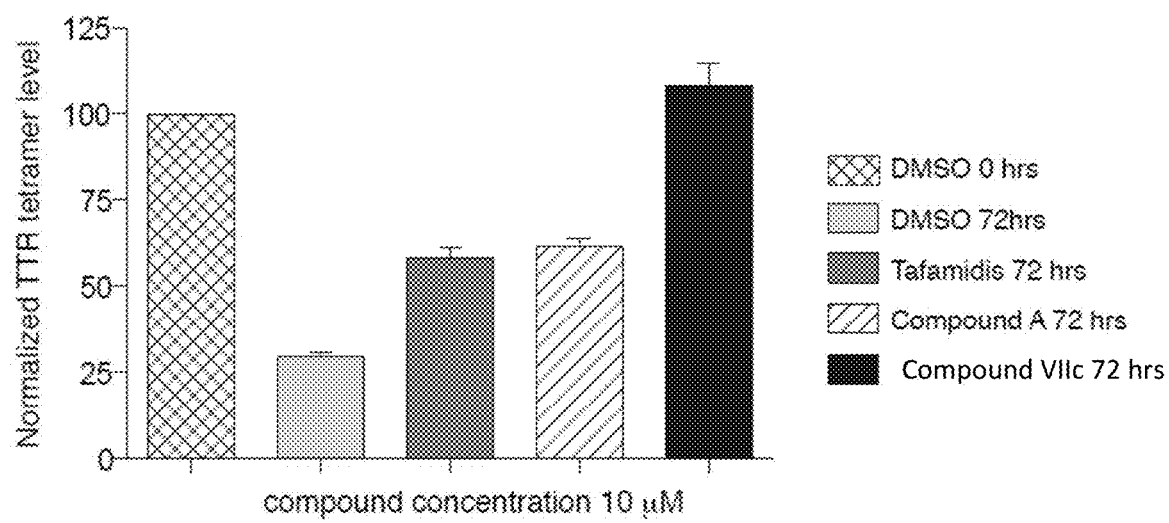
B
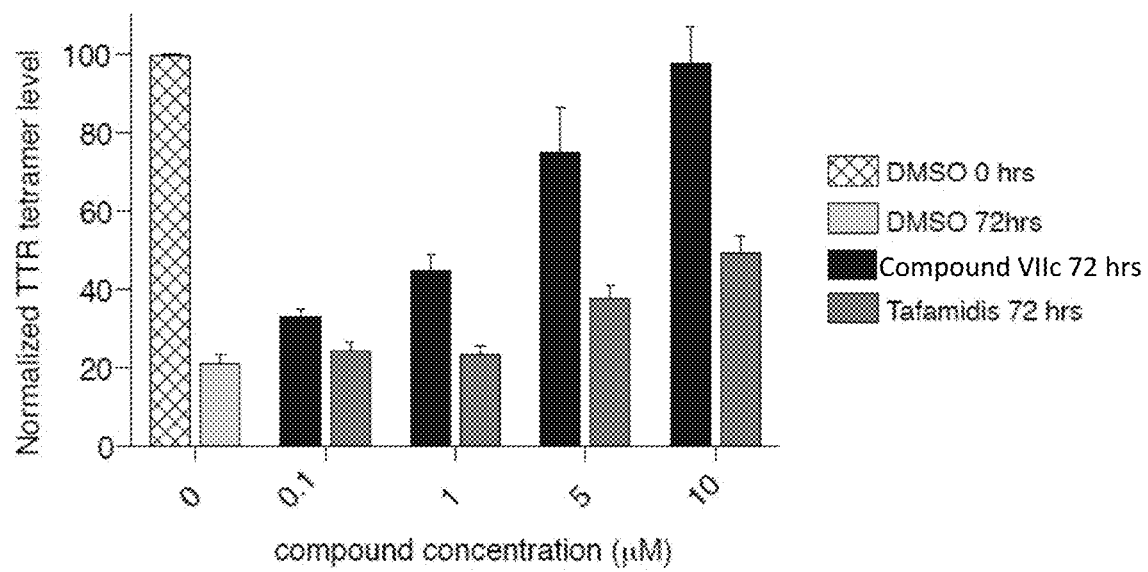

COMPOUNDS AND COMPOSITIONS THAT BIND AND STABILIZE TRANSTHYRETIN AND THEIR USE FOR INHIBITING TRANSTHYRETIN AMYLOIDOSIS AND PROTEIN-PROTEIN INTERACTIONS

CROSS-REFERENCE

This application is a continuation of application Ser. No. 15/883,750 filed Jan. 30, 2018, now U.S. Pat. No. 10,398,681, which is a continuation of application Ser. No. 15/480,139 filed Apr. 5, 2017, now U.S. Pat. No. 9,913,826, which is a continuation of application Ser. No. 14/876,447, filed on Oct. 6, 2015, now U.S. Pat. No. 9,642,838, which is a continuation of application Ser. No. 13/830,731, filed on Mar. 14, 2013, now U.S. Pat. No. 9,169,214, which claims the benefit of U.S. Provisional Patent Application No. 61/745,089, filed Dec. 21, 2012, which applications are incorporated herein by reference in their entirety.

INTRODUCTION

Protein aggregation underlies a large number of human disorders, including some of the most common diseases observed in the aging population, including systemic and CNS amyloidoses (Selkoe et al. *Nat Cell Biol* 6:1054-1061 (2004); Falk et al., *N. Engl. J. Med.* 337:898-909 (1997)). Recently this process has also been implicated as an important mechanism in cellular senescence (Haigis et al., *Mol Cell* 40:333-344 (2010)). Aggregation of disease-associated peptides or proteins can occur in different sub-cellular compartments and either affect specific tissues or spread systemically (Stefani et al., *Biochimica et biophysica acta* 1739:5-25 (2004)). Data from biophysical, cellular and animal models indicate that a number of genetic and environmental factors contribute to in vivo protein misfolding, aggregation and amyloid fibril formation (amyloidogenesis). Protein misfolding and amyloid formation is believed to be intimately involved in the pathogenic mechanisms of human amyloid diseases based on the demonstrated cytotoxicity of in vitro aggregated proteins/peptides. A number of observations in patients also indicate that amyloid formation is intimately linked to disease pathogenesis. Such observations include: lower levels of amyloid observed in the CNS of age-matched controls relative to Alzheimer disease patients and the correlation of improved health with the clearance of amyloid in Familial Amyloid polyneuropathy (FAP) patients, following liver transplantation to replace mutant TTR with wild-type TTR. Hence, there is strong interest in identifying ways to prevent the conformational changes that result in the formation of protein/peptide aggregates and amyloid formation.

Transthyretin (TTR or prealbumin) is one of more than 30 proteins whose aggregation can cause disease (Selkoe et al., *Nature* 426:900-904 (2003); Reixach et al., *Proc. Natl. Acad. Sci.* USA 101:2817-2822 (2004)). TTR is a 127-amino-acid, β-sheet-rich protein, which forms homotetramers, and is primarily synthesized by the liver and secreted into the blood. Using orthogonal binding surfaces TTR binds to both thyroxine ($T_4$) and holo retinol-binding protein (RBP). TTR is the main carrier of RBP, but due to the presence of two other $T_4$ transport proteins it is only a back-up carrier for $T_4$ in humans (<1% $T_4$ bound). The two $T_4$-binding pockets, which remain largely unoccupied in humans, are formed by the weaker dimer-dimer interface (Connelly et al., *Curr Opin Struct Biol* 20:54-62 (2010)). Each of the two $T_4$ binding sites created by the dimer-dimer interface of the TTR homotetramer consists of an outer binding subsite, an inner binding subsite, and an intervening interface that are composed of pairs of symmetric hydrophobic depressions referred to as halogen binding pockets (HBPs), in which the iodine atoms of $T_4$ reside (Wojtczak et al., *Acta Crystallogr D Biol Crystallogr,* 52 pp. 758-765 (1996)). Dissociation of the TTR-tetramer at the $T_4$-binding interface, which generates dimers that rapidly dissociate into amyloidogenic monomers, is the rate-limiting step during TTR misfolding and amyloid formation.

There are more than 100 known amyloidogenic mutations in TTR, which segregate into ethnic and geographic groupings (Saraiva et al., *Hum Mutat* 5:191-196 (1995); Connors et al., *Amyloid* 10:160-184 (2003)). Point mutations in TTR promote TTR amyloidogenesis either by lowering the thermodynamic stability of tetrameric TTR or through decreasing the kinetic barrier for tetramer dissociation, or both (Connelly et al., *Curr Opin Struct Biol* 20:54-62 (2010)). These mutations lead to hereditary TTR amyloidoses such as familial amyloid polyneuropathy (FAP) and familial amyloid cardiomyopathy (FAC), which are both autosomal dominant conditions with varying ages of onset and penetrance depending on ethnic background. One of the clinically most important FAP-causing TTR mutations is the thermodynamically destabilized Val30Met TTR (V30M) (Coelho *Curr Opin Neurol* 9:355-359 (1996)). However, the slow rate of tetramer dissociation (comparable to that of wild type TTR) limits the steady-state concentration of the destabilized amyloidogenic monomer, which might explain the incomplete penetrance of the V30M mutation in non-Portuguese populations. The most common TTR variant with almost exclusive cardiac involvement, is the kinetically destabilizing V122I mutation. Although the V122I-TTR monomer has similar stability to the wild type (WT-TTR) monomer, the tetramer dissociates 3-fold faster under physiological conditions and may explain the higher penetrance of the V122I mutation (Jiang et al., *Proc Natl Acad Sci USA* 98:14943-14948 (2001)). This allele occurs in 3-4% of African-Americans (~1.3 million people) and is hypothesized to contribute to the increased prevalence of heart failure among African Americans (Jacobson et al., *N Engl J Med* 336:466-473 (1997); Connors et al. *Am Heart J* 158:607-614 (2009); Buxbaum et al. *Am Heart J* 159:864-870 (2010)). WT-TTR aggregation underlies the development of senile systemic amyloidosis (SSA), a condition that affects up to 10-20% of the population over age 65.

Protein-protein interactions (PPIs) are a key regulatory mechanism for a number of physiological and pathological cellular processes making them prime targets for therapeutic intervention (Arkin et al, *Nat Rev Drug Discov.,* 2004 April; 3(4):301-17). Although therapeutic antibodies that block PPIs are the fastest growing segment of the prescription-drug market, no small-molecule therapeutics have yet been approved for this important target class. The majority of PPIs involve large interfaces, in many cases larger than 1500 Å$^2$ (up to 4500 Å$^2$) in which the affinity is obtained by a multitude of often weak interactions. As a consequence these widely spaced interactions are difficult to mimic with small molecules. Antagonizing PPIs with small, organic compounds is a challenging for a number of reasons: 1) a large, often flat, surface area is buried on each side of the interface, 2) the lack of deep cavities, 3) the nature of typical small-molecule libraries. Thus many PPIs have come to be considered 'undruggable'. Many extracellular PPI targets have been validated through the use of antibodies or other protein antagonists, some of which have become highly successful drugs. Examples are TNFa, IL2, IL4, IL13, VEGF, IFNa, SDF-1, CD4, MET, HER1&2.

The development of fluorescent and/or luminescent biosensors has emerged as a powerful tool for monitoring biomolecules in vitro and in vivo. Förster resonance energy transfer (FRET) is a method that measures distance-dependent energy transfer between two chromophores, one the donor and the other the acceptor (Gell et al, *Adv Exp Med Biol.* 2012; 747:19-41; Miyawaki A., *Annu Rev Biochem.* 2011 Jun. 7; 80:357-73). The donor, after excitation by light, can transfer energy to the acceptor via an induced dipole induced dipole interaction. The efficiency of the energy transfer depends on the sixth power of the distance between the dyes. In general, the acceptor must be at 10-80 A distance to the donor for efficient energy transfer. FRET is a useful technique because measurements can be under physiological conditions and is one of the most widely used sensing mechanisms for ratiometric fluorescent probes. It permits the investigation of protein/protein interactions and has proven to be a robust method for the investigation of the dynamics of protein complex composition and stoichiometry.

SUMMARY

Disclosed herein are compounds and compositions thereof, which find use in increasing the stability of proteins, particularly proteins that may misfold and form aggregates. Also provided herein are methods for using these compounds and compositions for increasing stability of proteins and thereby decreasing aggregate formation by these proteins. Also disclosed herein are heterobifunctional compounds that include a TTR binding compound connected to a targeting moiety via a linker, for use in disrupting PPIs of a target protein. Also disclosed herein are labeled compounds binding to the $T_4$ pocket of TTR, which are used to determine the concentration of stabilized and/or tetrameric TTR, either by measurement of retained label and/or by measurement of distance-dependent energy transfer between the labeled compound bound to the $T_4$ binding pocket and a labeled compound and/or peptide and/or protein bound to an orthogonal binding surface on the TTR tetramer.

Provided herein are methods for using the disclosed compounds to increase the stability of tetrameric TTR thereby preventing tetramer dissociation leading to TTR dimer and monomer misfolding, protein aggregation and the formation and deposition of TTR amyloid.

The TTR stabilizers disclosed herein may be used to decrease TTR amyloid formation and/or to decrease cell dysfunction and/or death associated with TTR amyloid formation. The TTR stabilizers may be used to decrease TTR amyloid formation in vitro in a cell-free system, in vitro—intra or extracellularily in cell culture, and in vivo, such as TTR found in bodily fluids, including but not restricted to blood, serum, cerebrospinal fluid, tissue and organs, including but not restricted to, the heart, the kidney, peripheral nerves, meninges, the central nervous system, the eye (including the retina and vitreous fluid) of a subject. As such, methods for using the disclosed compounds include administering the disclosed compounds in vitro, ex vivo or to a subject in vivo to increase the stability of TTR found in bodily fluids, including but not restricted to blood, serum, cerebrospinal fluid, tissues and organs, including but not restricted to, the heart, the kidney, peripheral nerves, meninges, the central nervous system, the eyes.

Also provided herein are methods for the treatment, prevention, delay or improvement of one or more symptoms of TTR amyloidoses as well as methods for the administration of a therapeutically effective amount of a compound provided herein. In one embodiment, the compound prevents dissociation of a transthyretin tetramer by stabilization of the TTR tetramer. The TTR amyloid diseases include, but are not limited to familial amyloid polyneuropathy, familial amyloid cardiomyopathy, leptomeningeal amyloidis, oculoleptomengial amyloidosis, senile systemic amyloidosis, vitreous amyloidosis, CNS amyloidsis. Other amyloid diseases include but are not restricted to ocular amyloidosis, gastrointestinal amyloidoses, neuropathic amyloidoses, non-neuropathic amyloidoses, nephropathy, non-hereditary amyloidoses, reactive/secondary amyloidoses, cerebral amyloidoses, Alzheimer's disease, spongiform encephalopathy (i.e. Creutzfeldt Jakob disease, GSS, fatal familial insomnia), frontotemporal dementia, Parkinson's disease, amyotrophic lateral sclerosis (ALS), Down Syndrome, multiple sclerosis, polyneuropathy, Guillain-Barré syndrome, macular degeneration, vitreous opacities, glaucoma, type II diabetes and medullary carcinoma of the thyroid.

BRIEF DESCRIPTION OF THE DRAWINGS

FIG. 1 depicts TTR ligands (10 μM) competitively displace the FP-probe 5 (0.2 μM) from TTR (0.4 μM) through binding to the $T_4$-binding sites (the lower the probe binding, the higher the binding affinity of TTR ligand).

FIG. 4 depicts fluorescence change due to modification of TTR in human serum by covalent probe 6 (A) monitored for 6 h in the presence of probe alone (black circles) or probe and TTR ligands (Compound VIIc, Compound A, and tafamidis) (colors) (B) percentage of covalent probe 6 binding to TTR in the presence of ligands (Compound VIIc, Compound A, and tafamidis) measured after 6 hours of incubation, relative to probe alone (The lower the binding of the probe the higher the binding selectivity of the ligand to TTR). Each bar shows the mean +/−SD of three replicates.

FIG. 5 depicts the stabilization of WT-TTR in serum against acid-mediated denaturation in (A) the presence of 10 microM Compound VIIc, Compound A, and tafamidis, (B) the presence of concentration range (0.1 to 10 microM) of Compound VIIc and Tafamidis. Serum samples were incubated in acetate buffer (pH 4.0), with DMSO or 10 μM of test compound, for the desired time period (0 and 72 hours) before cross-linking, SDS-PAGE, and immunoblotting. The density of all TTR bands (TTR tetramer; arrowhead and TTR bound to RBP; solid arrow) was quantified using an Odyssey infrared imaging system (LI-COR Bioscience, Lincoln, Nebr.) and reported as % TTR tetramer=100×[(tetramer & tetramer+RBP density, 72 hrs)/(tetramer & tetramer+RBP density of DMSO, 0 hrs)]. Each bar shows the mean +/−SD of three replicates.

Figure 6A:
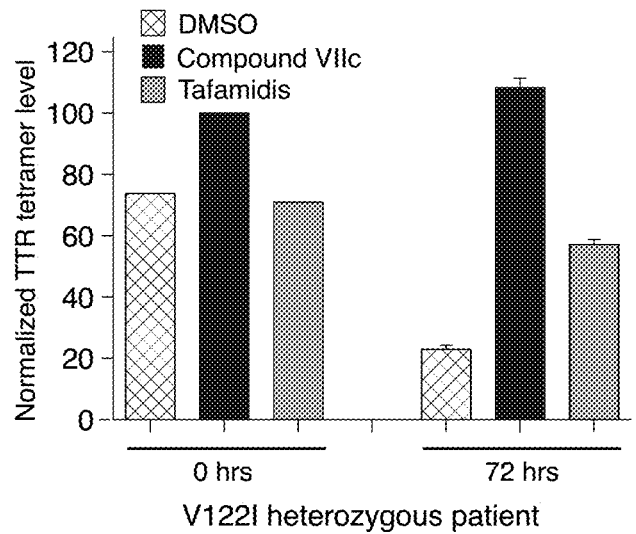
Figure 6B:
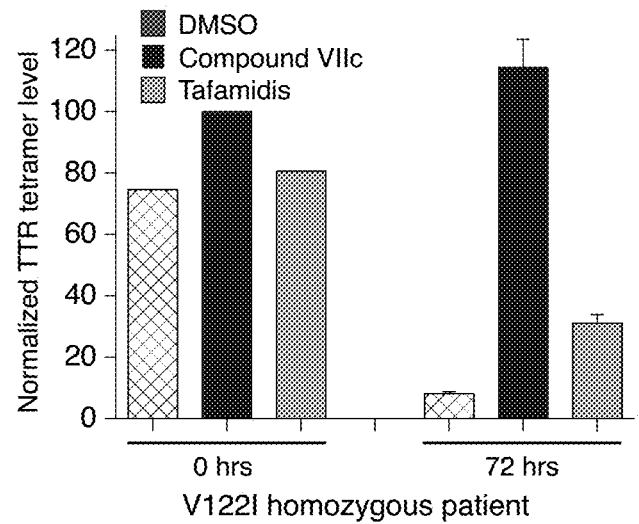

FIGS. 6A-6B illustrate the stabilization of V122I-TTR in serum from two FAC patients against acid-mediated denaturation in the presence of Compound VIIc and tafamidis. Serum samples were incubated in acetate buffer (pH 4.0), with DMSO or 10 μM of tafamidis and Compound VIIc, for the desired time period (0 and 72 hours) before cross-linking, SDS-PAGE, and immunoblotting. Each bar shows the mean +/−SD of three replicates.

Figure 7:
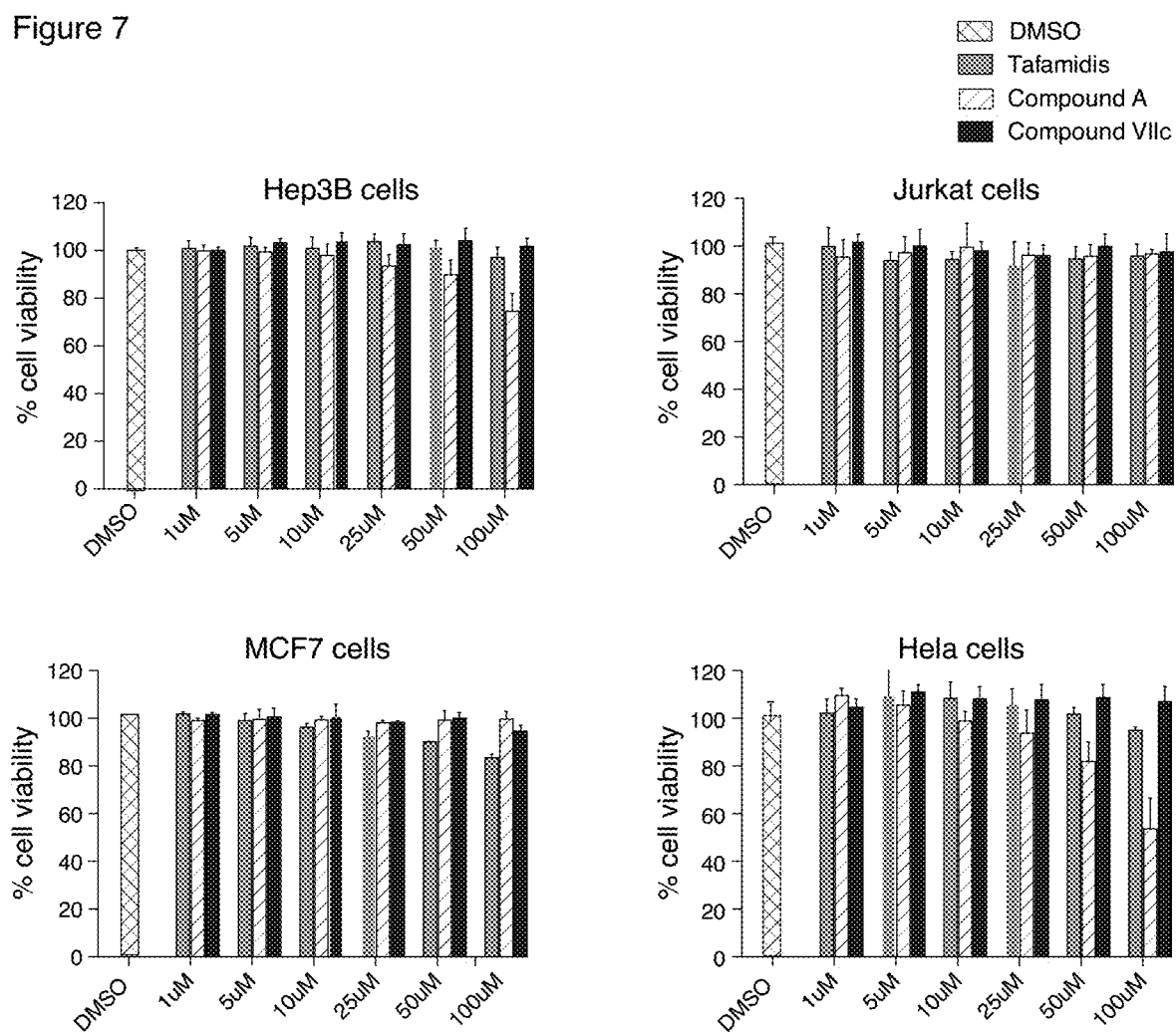

FIG. 7 depicts the assessment of the cytotoxicity of Compound VIIc, Compound A, and tafamidis, at concentrations from 1 to 100 μM, on four different cell lines: Hep3B: human hepatoma cell line; Jurkat: T lymphocyte cell line; MCF7: breast cancer cell line HeLa: cervical cancer cell line; Cell viability was assessed using the MTT assay after 24 h. Cell viability results are reported relative to cells treated with vehicle only (100% cell viability). Each bar shows the mean +/−SD of three replicates.

DEFINITIONS

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

The term "isolated compound" means a compound which has been substantially separated from, or enriched relative to, other compounds with which it occurs in nature or during chemical synthesis. Isolated compounds are usually at least about 80% pure, or at least about 90% pure, at least about 98% pure, or at least about 99% pure, by weight. The present invention is meant to encompass diastereomers as well as their racemic and resolved, enantiomerically pure forms and pharmaceutically acceptable salts thereof.

"Treating" or "treatment" of a condition or disease includes: (1) preventing, ameliorating or altering at least one symptom of the conditions in a beneficial manner, i.e., causing a clinical symptom to not significantly develop in a mammal that may be exposed to or predisposed to the disease but does not yet experience or display symptoms of the disease, (2) inhibiting the disease, i.e., arresting or reducing the development of the disease and/or its symptoms, or (3) relieving the disease, i.e., causing regression or cure of the disease or its clinical symptoms. As used herein, amelioration of the symptoms of a particular disorder by administration of a particular compound or pharmaceutical composition refers to any lessening of disease symptoms and/or progression, whether permanent or temporary or lasting or transient, that is or can be attributed to or associated with the administration of the subject compound or composition.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The terms "subject" and "patient" mean a mammal that may have a need for the pharmaceutical methods, compositions and treatments described herein. Subjects and patients thus include, without limitation, primate (including humans), canine, feline, ungulate (e.g., equine, bovine, swine (e.g., pig)), and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is preferably sterile, and free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

As used herein, pharmaceutically acceptable derivatives of a compound include salts, esters, enol ethers, enol esters, acetals, ketals, orthoesters, hemiacetals, hemiketals, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Pharmaceutically acceptable salts may also include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Other pharmaceutically acceptable salts include acid salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate; base salts including ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

Pharmaceutically acceptable esters include, but are not limited to, alkyl, alkenyl, alkynyl, and cycloalkyl esters of acidic groups, including, but not limited to, carboxylic acids, phosphoric acids, phosphinic acids, sulfonic acids, sulfinic acids and boronic acids.

Pharmaceutically acceptable enol ethers include, but are not limited to, derivatives of formula C=C(OR) where R is hydrogen, alkyl, alkenyl, alkynyl, or cycloalkyl. Pharmaceutically acceptable enol esters include, but are not limited to, derivatives of formula C=C(OC(O)R) where R is hydrogen, alkyl, alkenyl, alkynyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

The term "organic group" and "organic radical" as used herein means any carbon-containing group, including hydrocarbon groups that are classified as an aliphatic group, cyclic group, aromatic group, functionalized derivatives thereof and/or various combination thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, isopropyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, trifloromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include fluoro, chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl) carboxamide, trifluoromethyl, N—(($C_1$ to $C_6$ alkyl)sulfonyl) amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(iso-propyl)phenyl, 2, 3, or 4-ethylphenyl, 2, 3 or 4-(n-propyl)phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy) phenyl group such as 2, 3 or 4-carboxyphenyl or 2,4-di (protected carboxy)phenyl; a mono- or di(hydroxymethyl) phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl) ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature or element may, but need not, occur, and that the description includes instances where the event or circumstance occurs and instances in which it does not. For example, "heterocyclo group optionally mono- or di- substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)- stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

DETAILED DESCRIPTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that and in the appended claims, the singular forms "a," "an," and "the" include plural referents unless the context clearly dictates otherwise. Thus, for example, reference to "a method" includes a plurality of such methods and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., -J, =W—, —X=, =Y—, —Z=, -Q, —$R^{V1}$, —$R^{V2}$, —$R^{V3}$, —$R^{V4}$, —$R^T$, —$R^{TT}$, -$Q^{CA}$, -$Q^{HA}$, —$R^{PP}$, —$R^R$, —$R^{RA}$, -$L^R$-, -$M^R$, —$R^K$, —$R^{RR}$, —$R^J$, -$M^J$, —$R^N$, —$R^{J1}$, —$R^{J2}$, —$R^{J3}$, —$R^{J4}$, —$R^{J5}$, —$R^{J6}$, -$L^J$-, —$R^{J2X}$, —$R^{J2XX}$, —$R^{JJ}$, —$R^{JJJ}$, -$L^{JJJ}$-, —$R^{P2}$, —$R^{P3}$, —$R^{P4}$, —$R^{P5}$, —$R^{P6}$, —$R^{P2R}$, —$R^{P2RA}$, —$R^{P3R}$, —$R^{P3RA}$, —$R^{P4R}$, —$R^{P4RA}$, —$R^{P5R}$, —$R^{P5RA}$, —$R^{P6R}$, —$R^{P6RA}$, —$R^{AK}$, etc.) are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Overview

The present disclosure is based on the identification of compounds that bind to a TTR tetramer in the presence of a TTR ligand known to bind and stabilize TTR tetramer. These compounds stabilize TTR tetramers and thereby reduce the formation of TTR amyloid. These compounds also find use to determine the level of stabilized and/or tetrameric TTR. In addition, these compounds find use in the preparation of heterobifunctional compounds that recruit TTR for use in disrupting PPIs.

Compositions

Provided herein are compounds that may be used to stabilize TTR tetramers reducing TTR amyloid formation. These compounds can be incorporated into a variety of formulations for therapeutic administration by a variety of routes, including but not limited to oral, parenteral, transdermal, intrathecal, ophthalmic, topical, pulmonary, nasal, rectal or depot administration.

More particularly, the compounds disclosed herein can be formulated into pharmaceutical compositions by combination with appropriate, pharmaceutically acceptable carriers, diluents, excipients and/or adjuvants.

Compounds

In some embodiments, a compound of the invention is of the structure of Compound Ia:

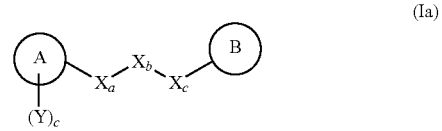

(Ia)

where $X_a$, $X_b$ and $X_c$ are independently selected from $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

the A ring is a 4 to 12-membered ring, in certain embodiments the 4 to 12-membered ring is an aromatic or heteroaromatic ring;

each Y is independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano;

c is a number from zero to 5; and the B ring is a hetercyclic ring selected from the following (h1-h30):

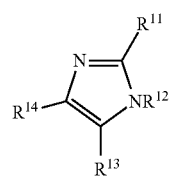
h1

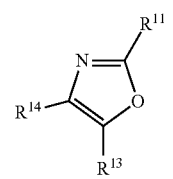
h2

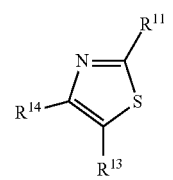
h3

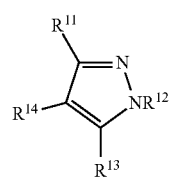
h4

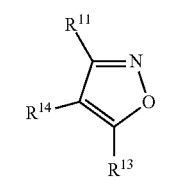
h5

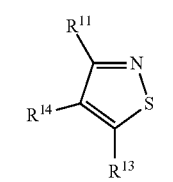
h6

-continued

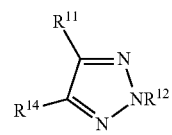
h7

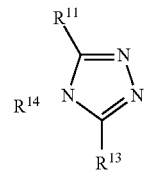
h8

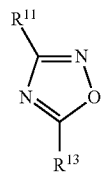
h9

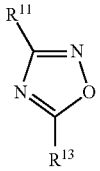
h10

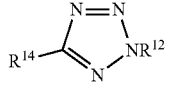
h11

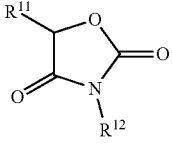
h12

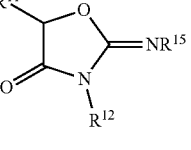
h13

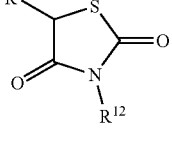
h14

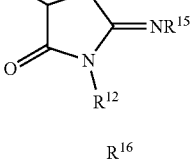
h15

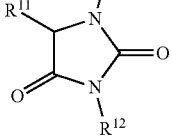
h16

-continued h17 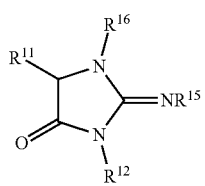

h18 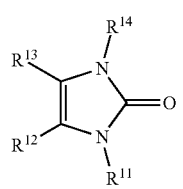

h19 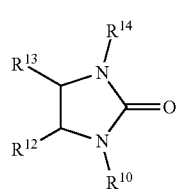

h20 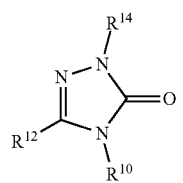

h21 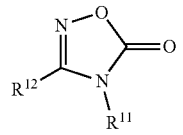

h22 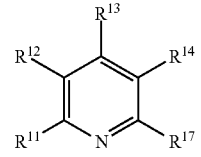

h23 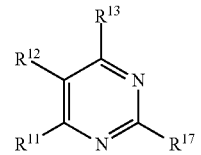

h24 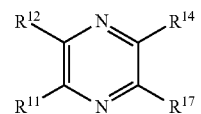

h25 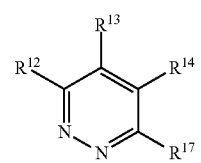

-continued h26 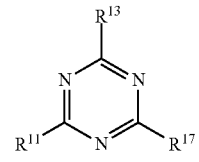

h27 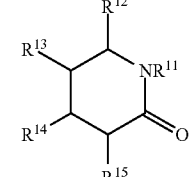

h28 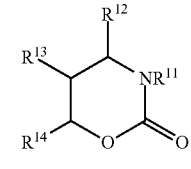

h29 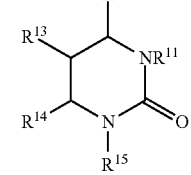

h30 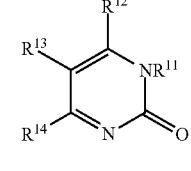

where $R^{11}$—$R^{16}$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano; and $R^{17}$ is selected from a hydroxyl, alkyl, amino, and alkyl amino;

or a pharmaceutically acceptable salt, ester, enol ether, enol ester, amide, acetal, ketal, orthoester, hemiacetal, hemiketal, hydrate, solvate or prodrug thereof.

In some embodiments, a compound of the invention is of the structure of Compound Ib:

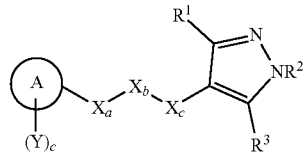

(Ib)

where $R^1$ and $R^3$ are independently selected from hydrogen, alkyl, substituted alkyl, alkenyl, substituted alkenyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

$R^2$ is selected from hydrogen, alkyl, substituted alkyl, aryl, substituted aryl, alkoxy, aryloxy, hydroxyl, a heterocyclic group, acyl, substituted acyl, alkoxycarbonyl, substituted alkoxycarbonyl, acylamino, substituted acylamino, thioalkyl and cyano;

$X_a$, $X_b$ and $X_c$ are independently selected from $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

the A ring is a 4 to 12-membered ring, in certain embodiments the 4 to 12-membered ring is an aromatic or heteroaromatic ring;

each Y is independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano; and c is a number from zero to 5;

or a pharmaceutically acceptable salt, ester, enol ether, enol ester, amide, acetal, ketal, orthoester, hemiacetal, hemiketal, hydrate, solvate or prodrug thereof.

In some embodiments, a compound of the invention is of the structure of Compound IIa:

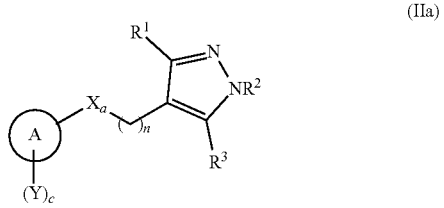

(IIa)

where n is 1 to 8;

$R^1$, $R^2$ and $R^3$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

$X_a$ is $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

the A ring is a 5 to 12-membered ring, in certain embodiments the 5 to 12-membered ring is an aromatic or heteroaromatic ring;

each Y is independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano; and c is a number from zero to 5;

or a pharmaceutically acceptable salt, ester, enol ether, enol ester, amide, acetal, ketal, orthoester, hemiacetal, hemiketal, hydrate, solvate or prodrug thereof.

In some embodiments, a compound of the invention is of the structure of Compound IIb:

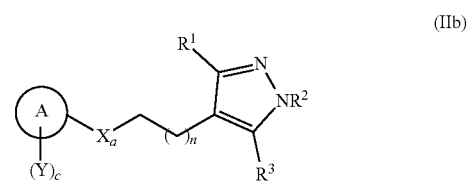

(IIb)

where n is zero to 7;

$R^1$, $R^2$ and $R^3$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

$X_a$ is $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

the A ring is a 5 to 12-membered ring, in certain embodiments the 5 to 12-membered ring is an aromatic ring;

each Y is independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano; and c is a number from zero to 5;

or a pharmaceutically acceptable salt, ester, enol ether, enol ester, amide, acetal, ketal, orthoester, hemiacetal, hemiketal, hydrate, solvate or prodrug thereof.

In some embodiments, a compound is of the structure of Compound IIIa:

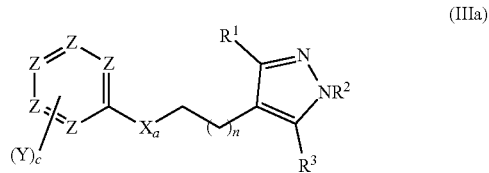

(IIIa)

where n is zero to 7;

Z is carbon or up to three of the five Z may be nitrogen with the remaining being carbon;

$R^1$, $R^2$ and $R^3$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

$X_a$ is $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

each Y is independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano; and c is a number from zero to 5;

or a pharmaceutically acceptable salt, ester, enol ether, enol ester, amide, acetal, ketal, orthoester, hemiacetal, hemiketal, hydrate, solvate or prodrug thereof.

In some embodiments, a compound is of the structure of Compound IIIb:

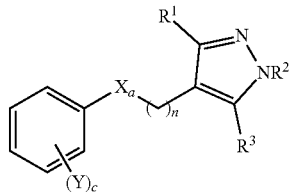

(IIIb)

where n is 1 to 8;

$R^1$, $R^2$ and $R^3$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

$X_a$ is $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

each Y is independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, sulfonamide, sulfonyl fluoride, thioester and cyano; and c is a number from zero to 5;

or a pharmaceutically acceptable salt, ester, enol ether, enol ester, amide, acetal, ketal, orthoester, hemiacetal, hemiketal, hydrate, solvate or prodrug thereof.

In some embodiments, a compound is of the structure of Compound IIIb:

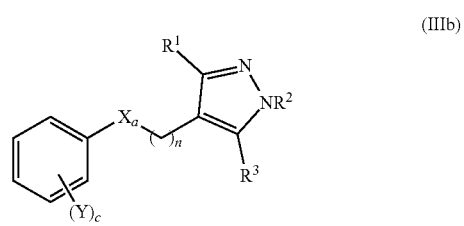

(IIIb)

where n is 1 to 4;

$R^1$ is a short chain alkyl having 1 to 4 carbon atoms;

$R^2$ is hydrogen;

$R^3$ is a short chain alkyl having 1 to 4 carbon atoms;

$X_a$ is $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

each Y is independently selected from a halogen, acyl, substituted acyl, carboxyl, heterocyclic group, alkoxycarbonyl and substituted alkoxycarbonyl; and c is 2;

or a pharmaceutically acceptable salt, ester, enol ether, enol ester, acetal, amide, ketal, orthoester, hemiacetal, hemiketal, hydrate, solvate or prodrug thereof.

In some embodiments, a compound of the invention is of the structure of Compound IVa:

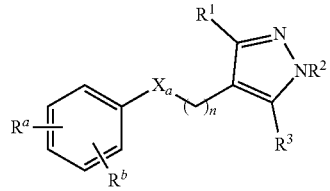

(IVa)

where n is 1 to 8;

$R^1$, $R^2$ and $R^3$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halo, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

$X_a$ is $C(R^4)(R^5)$, O, N—$R^5$ or S; where $R^4$ and $R^5$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

$R^a$ is CHO, COOH, COOR$^6$, CONR$^7$R$^8$, tetrazolyl, CONHOH, B(OH)$_2$, CONHSO$_2$Ar, CONHCH(R$^9$)COOH, hydrogen, halogen, alkyl, substituted alkyl, acyl, substituted acyl, carboxyl, heterocyclic group, sulfonamide, sulfonyl fluoride, thioester, alkoxycarbonyl or substituted alkoxycarbonyl;

$R^b$ is CHO, COOH, COOR$^6$, CONR$^7$R$^8$, tetrazolyl, CONHOH, B(OH)$_2$, CONHSO$_2$Ar, CONHCH(R$^9$)COOH, hydrogen, halogen, alkyl, substituted alkyl, acyl, substituted acyl, carboxyl, heterocyclic group, sulfonamide, sulfonyl fluoride, thioester, alkoxycarbonyl or substituted alkoxycarbonyl;

$R^6$ is alkyl, haloalkyl, cycloalkyl, or heterocyclyl;

$R^7$ and $R^8$ are each independently hydrogen, alkyl, alkenyl, alkynyl, cycloalkyl, heterocyclyl, or heteroaryl; and $R^9$ is the side chain of a naturally occurring α-amino carboxylic acid;

or a pharmaceutically acceptable salt, ester, enol ether, enol ester, amide, acetal, ketal, orthoester, hemiacetal, hemiketal, hydrate, solvate or prodrug thereof.

In some embodiments, a compound of the invention is of the structure of Compound V:

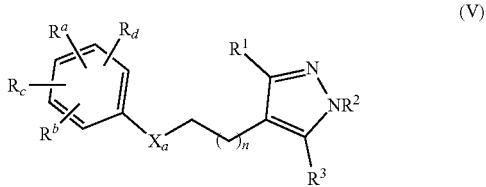

(V)

where n is zero to 7;

$R^1$, $R^2$ and $R^3$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halo, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

$X_a$ is C(R$^4$)(R$^5$), O, N—R$^5$ or S; where R$^4$ and R$^5$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

$R^a$ and $R^b$ are independently selected from CHO, COOH, COOR$^6$, CONR$^7$R$^8$, tetrazolyl, CONHOH, B(OH)$_2$, CONHSO$_2$Ar, CONHCH(R$^9$)COOH, CONHSO$_2$R$^{10}$, hydrogen, halogen, alkyl, substituted alkyl, acyl, substituted acyl, carboxyl, heterocyclic group, sulfonamide, sulfonyl fluoride, thioester, alkoxycarbonyl or substituted alkoxycarbonyl;

$R^c$ and $R^d$ are independently selected from hydrogen, halogen, alkyl, substituted alkyl, acyl, substituted acyl, carboxyl, heterocyclic group, sulfonamide, sulfonyl fluoride, thioester, trifluoromethyl, amino, substituted amino, sulfonyl, substituted sulfonyl, hydroxyl, alkoxycarbonyl or substituted alkoxycarbonyl;

$R^6$ is alkyl, haloalkyl, cycloalkyl, or heterocyclyl;

$R^7$, $R^8$ and $R^{10}$ are each independently hydrogen, alkyl, alkenyl, alkynyl, cycloalkyl, heterocyclyl, or heteroaryl; and $R^9$ is the side chain of a naturally occurring α-amino carboxylic acid;

or a pharmaceutically acceptable salt, ester, enol ether, enol ester, amide, acetal, ketal, orthoester, hemiacetal, hemiketal, hydrate, solvate or prodrug thereof.

In some embodiments, a compound of the invention is of the structure of Compound VI:

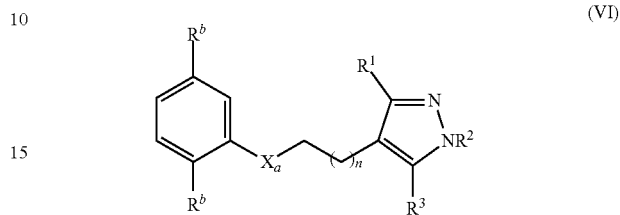

(VI)

where n is 2;

$R^1$ is a short chain alkyl having 1 to 4 carbon atoms;

$R^2$ is hydrogen;

$R^3$ is a short chain alkyl having 1 to 4 carbon atoms;

$X_a$ is C(R$^4$)(R$^5$), O, N—R$^5$ or S; where R$^4$ and R$^5$ are independently selected from hydrogen, alkyl, substituted alkyl, alkenyl, substituted alkenyl, alkynyl, substituted alkynyl, aryl, substituted aryl, alkoxy, aryloxy, hydroxyl, a heterocyclic group, halogen, nitro; acyl, substituted acyl, carboxyl, alkoxycarbonyl, substituted alkoxycarbonyl, aminoacyl, substituted aminoacyl, amino, substituted amino, acylamino, substituted acylamino, and cyano;

$R^a$ is CHO, COOH, COOR$^6$, CONR$^7$R$^8$, tetrazolyl, CONHOH, B(OH)$_2$, CONHSO$_2$Ar, CONHCH(R$^9$)COOH, hydrogen, an acyl, substituted acyl, carboxyl, heterocyclic group, sulfonamide, sulfonyl fluoride, thioester, alkoxycarbonyl and substituted alkoxycarbonyl;

$R^b$ is CHO, COOH, COOR$^6$, CONR$^7$R$^8$, tetrazolyl, CONHOH, B(OH)$_2$, CONHSO$_2$Ar, CONHCH(R$^9$)COOH, a halogen, heterocyclic group, or hydrogen;

$R^6$ is alkyl, haloalkyl, cycloalkyl, or heterocyclyl;

$R^7$ and $R^8$ are each independently hydrogen, alkyl, alkenyl, alkynyl, cycloalkyl, heterocyclyl, or heteroaryl; and $R^9$ is the side chain of a naturally occurring α-amino carboxylic acid;

or a pharmaceutically acceptable salt, ester, enol ether, enol ester, amide, acetal, ketal, orthoester, hemiacetal, hemiketal, hydrate, solvate or prodrug thereof.

In some embodiments, a compound of the invention is of the structure of Compound VIIa:

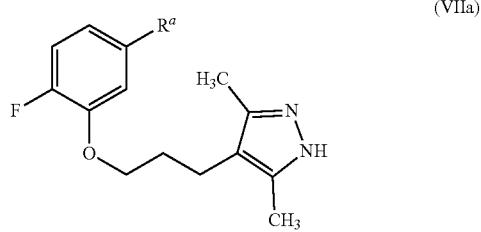

(VIIa)

where $R^a$ is OH, CHO, COOH, CONH$_2$, CONH(OH), COOR$^6$, CONHR$^6$; and $R^6$ is straight of branched alkyl of 1-3 carbon atoms;

or a pharmaceutically acceptable salt, ester, enol ether, enol ester, amide, acetal, ketal, orthoester, hemiacetal, hemiketal, hydrate, solvate or prodrug thereof.

In some embodiments, a compound of the invention is of the structure of Compound VIIb:

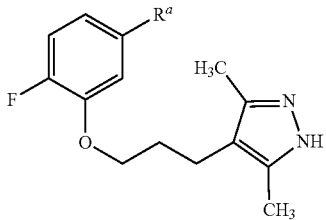

(VIIb)

where $R^a$ is COOH, CONH$_2$, CONH(OH), COOR$^6$, CONHR$^6$; and $R^6$ is straight of branched alkyl of 1-3 carbon atoms;

or a pharmaceutically acceptable salt, ester, enol ether, enol ester, amide, acetal, ketal, orthoester, hemiacetal, hemiketal, hydrate, solvate or prodrug thereof.

In some embodiments, a compound of the invention is of the structure of Compound VIIc:

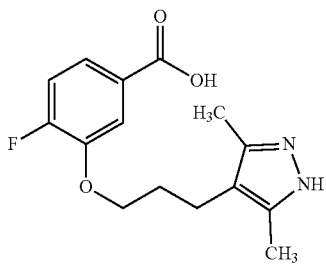

(VIIc)

or a pharmaceutically acceptable salt, ester, enol ether, enol ester, amide, acetal, ketal, orthoester, hemiacetal, hemiketal, hydrate, solvate or prodrug thereof.

Bifunctional Compounds for Disrupting PPIs

Also provided are heterobifunctional compounds that include a recruitment moiety connected to a targeting moiety via a linker. The recruitment moiety is a ligand of an abundant serum protein (e.g., a TTR binding compound of the disclosure, as described above). The targeting moiety is a ligand for a protein target of interest. In some embodiments, the protein target is involved in a protein protein interaction (PPI) where disruption of the PPI is desirable. For example, the PPI may be important in the regulation of a biological process that leads to a particular disease condition, where disrupting the PPI of interest may provide a method of inhibiting or treating the disease condition.

In some embodiments, the heterobifunctional compound is of the formula R-L-T, where the recruitment moiety R is a TTR-binding compound described by a structure of Compounds Ia-VIIc, above; L is a linker; and T is a targeting moiety. In some cases, the subject heterobifunctional compound includes one or more, such as two or more, recruitment moieties.

The recruitment moiety is connected to the targeting moiety via a linker, at any convenient point of attachment, which may be readily selected by one of ordinary skill in the art such that the binding property of the ligand to its cognate protein is not significantly reduced. In the TTR binding compounds described above, the position at which a linker may be connected using any convenient chemical modification chemistries is determined using any convenient selection method, such as but not limited to, modeling a X-ray crystal structure of TTR (e.g., a co-crystal structure of TTR with a ligand) to determine the mode of binding of the recruitment moiety to TTR and to select one or more appropriate positions which are not involved in contacts with the protein (e.g., solvent exposed positions), and which may be readily chemically modified. Further methods include determining whether a modification of interest has an adverse effect of the binding of the recruitment moiety to TTR using an in vitro binding assay.

Any convenient targeting moiety may be used. The targeting moiety may be a small molecule that targets a therapeutic protein target of interest. For example, the targeting moiety may be any convenient binder to a protein of a target ligand/receptor pair, such as but not limited to, IL2/IL2Rα, TNFα/TNFR1, VEGF-VEGFR, CCL12-CXCR4, CD4-gp 120, c-Met-HGF, and LFA-1-CD54. Suitable positions of the targeting moieties described above, to which a linker may be attached are selected using any convenient method, such as but not limited to, modeling methods using a X-ray crystal structure of the target protein (e.g., a co-crystal structure of target protein bound with the ligand) to model the mode of binding of the targeting moiety and to select appropriate positions that are not involved in contacts with the target protein (e.g., solvent exposed positions), and which may be readily chemically modified. For example, co-crystal structures of the IL-2 and TNF-alpha ligands are available for use in selecting convenient sites in these targeting moieties for chemical modification and attachment of linkers in preparation of subject heterobifunctional compounds. Further methods include determining whether a modification of interest has an adverse effect of the binding of the targeting moiety to the target protein using an in vitro binding assay.

Exemplary modifications of IL-2 and TNF-α targeting moieties of interest that may be used to attach targeting moieties to linkers in heterobifunctional compounds are shown below:

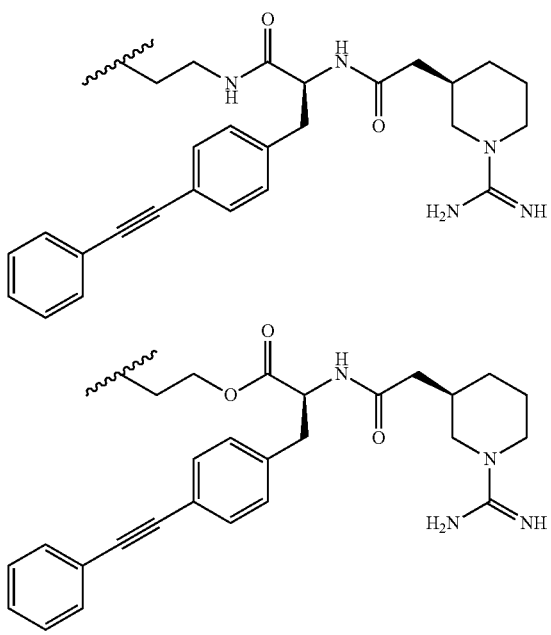

-continued

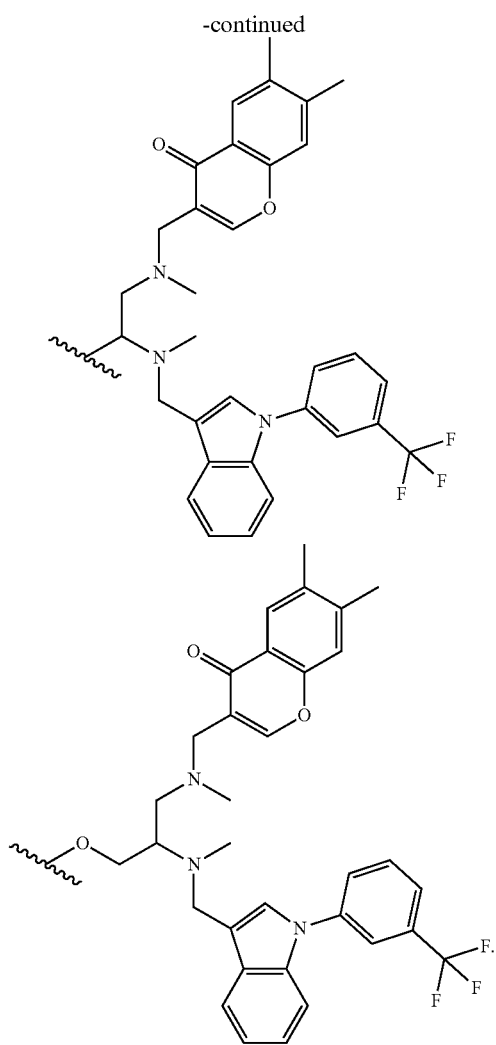

As used herein, the term "linker", "linkage" and "linking group" refers to a linking moiety that connects two groups and has a backbone of 20 atoms or less in length. A linker or linkage may be a covalent bond that connects two groups or a chain of between 1 and 20 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol); ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

The linking moiety may be conjugated to the recruitment and targeting moieties using any convenient functional groups (carboxylic acids, amines, alcohols, carbamates, esters, ethers, thioethers, maleimides, and the like), and linking chemistries. For example, any convenient conjugation chemistry described by G. T. Hermanson ("Bioconjugate Techniques", Academic Press, Second Edition, 2008) may be readily adapted for use in preparing the subject heterobifunctional compounds.

Exemplary linkers that may be used in connecting the recruitment moiety to the targeting moiety using any convenient chemical modification methods are shown below:

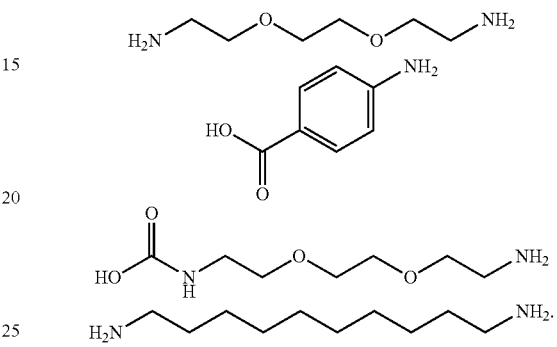

Formulation of Pharmaceutical Compositions

The pharmaceutical compositions provided herein contain therapeutically effective amounts of one or more of the compounds provided herein that are useful in the prevention, treatment, or amelioration of one or more of the symptoms of diseases or disorders associated with transthyretin (TTR) misfolding, or in which TTR misfolding is implicated, in a pharmaceutically acceptable carrier. Diseases or disorders associated with TTR misfolding include, but are not limited to, familial amyloid polyneuropathy, familial amyloid cardiomyopathy, senile systemic amyloidosis, Alzheimer's disease, spongiform encephalopathy (i.e., Creutzfeldt Jakob disease GSS, fatal familial insomnia), frontotemporal dementia, Parkinson's disease amyotrophic lateral sclerosis (ALS), Down Syndrome, multiple sclerosis, polyneuropathy, Guillain-Barrésyndrome, macular degeneration, vitreous opacities, glaucoma, type II diabetes or medullary carcinoma of the thyroid. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126). In certain preferable embodiments, the compounds are formulated into suitable pharmaceutical preparations for oral administration to a subject.

In the compositions, effective concentrations of one or more compounds or pharmaceutically acceptable derivatives thereof are mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with TTR misfolding or in which TTR misfolding is implicated.

In certain embodiments, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with TTR misfolding or in which TTR misfolding is implicated, as described herein.

In one embodiment, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using surfactants, such as TWEEN™, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Dosage forms or compositions containing active ingredient in the range of 0.005% to 100% with the balance made up from non-toxic carrier may be prepared. Methods for preparation of these compositions are known to those skilled in the art. For example, subject compositions may contain 0.001%-100% active ingredient, in one embodiment 0.1-95%, in another embodiment 75-85%.

Compositions for Oral Administration

Oral pharmaceutical dosage forms may be solid, gel or liquid. In certain embodiments, the solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545, the disclosures of which are herein incorporated by reference. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603, the disclosures of which are herein incorporated by reference. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include sodium chloride injection, Ringers injection, isotonic dextrose injection, sterile water injection, dextrose and lactated Ringers injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEENa 80). Sequestering or chelating agents of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle.

The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4.degree. C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. Where compositions are formulated as aerosols for inhalation or administration to the respiratory tract, the particles of the formulation may have diameters of 50 microns or less, such as 40 microns or less, such as 30 microns or less, such as 25 microns or less, such as 15 microns or less, such as 10 microns or less, such as 5 microns or less and including having diameters of 1 micron or less.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, such as for example for ophthalmic use, may be formulated as 0.01%-10% isotonic solutions, pH about 5-7, with appropriate salts.

Compositions for Other Routes of Administration

Other routes of administration, such as transdermal patches, including iontophoretic and electrophoretic devices, and buccal and rectal administration, are also contemplated herein.

Transdermal patches, including iotophoretic and electrophoretic devices of interest may include, but are not limited to those disclosed in U.S. Pat. Nos. 6,267,983, 6,261,595, 6,256,533, 6,167,301, 6,024,975, 6,010,715, 5,985,317, 5,983,134, 5,948,433, and 5,860,957, the disclosures of which are herein incorporated by reference.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. Examples of targeting methods of interest may include but are not limited to those described in U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, the disclosures of which are herein incorporated by reference.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811, the disclosure of which is herein incorporated by reference. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Dosages of the Compounds of the Present Disclosure

Depending on the subject and condition being treated and on the administration route, the subject compounds may be administered in dosages of, for example, 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from one to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is one which provides up to about 1 µg to about 1,000 µg or about 10,000 µg of subject composition to reduce a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

As discussed below, the present disclosure includes compounds and pharmaceutical compositions for stabilizing transthyretin and prevents dissociation of the transthyretin tetramer by kinetic stabilization of the native state of the transthyretin tetramer of TTR such as those found in the blood, serum, cerebrospinal fluid, fluids of the central nervous system (CNS), retina and the eyes. As such, compounds and pharmaceutical compositions of interest include those, which are compatible with the biological fluids of blood, serum, cerebrospinal fluid, fluids of the central nervous system, retina and the eyes.

Combination Therapy

For use in the subject methods, the subject compounds may be formulated with or otherwise administered in combination with other pharmaceutically active agents, including other agents, which may modulate intra or extracellular protein homeostasis and/or protein stability and or protein aggregation and/or protein folding, such as resveratrol, heat shock proteins, protein chaperones, and mimics thereof.

The compounds described above may also be administered in combination with other therapies for diseases caused by TTR amyloid. Therapies for diseases caused by TTR amyloid include heart transplant for TTR cardiomyopathy, liver transplant, other kinetic stabilizers of TTR, RNA knock-down and/or RNA interference methods and the like.

The compound described above may be administered before, after, or during another therapy for diseases caused by TTR amyloid.

The compounds described herein for use in combination therapy with the compounds of the present invention may be administered by the same route of administration (e.g. intrapulmonary, oral, enteral, etc.) that the compounds are administered. In the alternative, the compounds for use in combination therapy with the compounds of the present invention may be administered by a different route of administration that the compounds are administered.

The compounds and compositions provided herein may be administered as the only therapeutic agent or in combination with other active ingredients. For example, the compounds and compositions may be administered in combination with other compounds to treat amyloidoses and amyloid disorders, including but not limited to compounds that bind to and stabilize TTR and/or compounds that target TTR RNA and/or compounds that modulate the expression of the TTR protein and/or compounds that modulate the transcription of the TTR gene and/or compounds, which may modulate intra or extracellular protein homeostasis and/or protein stability and/or protein aggregation and/or protein folding.

Further active ingredients for combination therapy include but are not restricted to compounds for the disease modifying or symptomatic treatment of amyloidoses, including but not limited to familial amyloid polyneuropathy, familial amyloid cardiomyopathy, cerebral amyloidoses, leptomeningeal amyloidis, oculoleptomengial amyloidosis, senile systemic amyloidosis, vitreous amyloidosis, ocular amyloidoses, gastrointestinal amyloidoses, neuropathic amyloidoses, non-neuropathic amyloidoses, nephropathy, non-hereditary amyloidoses, reactive/secondary amyloidoses, Alzheimer's disease, spongiform encephalopathy (i.e.Creutzfeldt Jakob disease, GSS, fatal familial insomnia), Guillain-Barrésyndrome, frontotemporal dementia, multiple sclerosis, polyneuropathy, Parkinson's disease, amyotrophic lateral sclerosis (ALS), Down Syndrome, macular degeneration, vitreous opacities, glaucoma, type II diabetes and medullary carcinoma of the thyroid.

Kits

Kits with unit doses of the subject compounds, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Articles of Manufacture

The compounds or pharmaceutically acceptable derivatives may be packaged as articles of manufacture containing packaging material, a compound or pharmaceutically acceptable derivative thereof provided herein, which is effective for modulating TTR folding, or for treatment, prevention or amelioration of one or more symptoms of TTR mediated diseases or disorders, or diseases or disorders in which TTR misfolding, is implicated, within the packaging material, and a label that indicates that the compound or composition, or pharmaceutically acceptable derivative thereof, is used for modulating TTR folding, or for treatment, prevention or amelioration of one or more symptoms of TTR mediated diseases or disorders, or diseases or disorders in which TTR misfolding is implicated.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which TTR misfolding is implicated as a mediator or contributor to the symptoms or cause.

Methods

There are a number of published and well established in vitro assays that are used to evaluate the ability of test compounds to stabilize the TTR tetramers or prevent TTR fibrils formation. Examples include, but are not limited to, fluorescence polarization assay, fluorescent probe binding assay, isothermal titration calorimetry assay, fibril formation assay, determination of the three-dimensional structure of ligand bound to TTR using X-ray crystallography, FRET, kinetics of transthyretin tetramer dissociation or fibril formations, immunoblots to evaluate the stabilizing effect and selectivity of compound binding to TTR in serum.

Provided herein are methods for using the disclosed compounds to increase the stability of TTR thereby preventing it from misfolding, aggregating and forming TTR amyloid.

The TTR stabilizers disclosed herein may be used to decrease TTR amyloid formation and/or to decrease cell dysfunction and/or death associated with TTR amyloid formation. The TTR stabilizers may be used to decrease TTR amyloid formation in vitro in a cell-free system, in vitro—intra or extracellularily in cell culture, and in vivo, such as TTR found in bodily fluids including but not restricted to blood, serum, cerebrospinal fluid, tissue and organs including but not restricted to the heart, the kidney, peripheral nerves, meninges, the central nervous system, the eye (including the retina and vitreous fluid) of a subject. As such, methods for using the disclosed compounds include administering the disclosed compounds in vitro, ex vivo or to a subject in vivo to increase the stability of TTR found in bodily fluids including but not restricted to blood, serum, cerebrospinal fluid, tissues and organs including but not restricted to the heart, the kidney, peripheral nerves, meninges, the central nervous system, the eyes.

Amyloid fibril formation may be determined using a turbidity assay in vitro in a cell-free system. The turbidity assay can use a wild-type TTR or a mutant of TTR with an increased tendency to form amyloid fibrils. When a wild-type TTR is used TTR amyloidogenesis may be initiated by acidification of TTR or the addition of urea. When a mutant of TTR with an increased tendency to form amyloid fibrils, acidification of TTR or addition of urea may also be used.

TTR stabilizers disclosed herein may be used to decrease TTR amyloid formation in bodily fluids including but not restricted to blood, serum, cerebrospinal fluid, tissue and organs including but not restricted to the heart, the kidney, peripheral nerves, meninges, the central nervous system, the eye (including the retina and vitreous fluid) of a subject.

Also provided are methods for the stabilization of terameric transthyretin in a tissue or in a biological fluid, and thereby inhibiting and/or reducing dissociation and/or misfolding of TTR monomers. Generally, the method comprises administering to the tissue or biological fluid a composition comprising a stabilizing amount of a compound described herein that binds to transthyretin and prevents dissociation of the transthyretin tetramer by kinetic stabilization of the native state of the transthyretin tetramer. As such, methods for using the disclosed compounds include administering to the tissue or biological fluid a composition comprising a stabilizing amount of a compound described herein that binds to transthyretin and prevents dissociation of the transthyretin tetramer by kinetic stabilization of the native state of the transthyretin tetramer of TTR found in the blood, serum, cerebrospinal fluid, fluids of the central nervous system, retina and the eyes. Generally, the method involves administering to the tissue or biological fluid a stabilizing amount of a compound provided herein that binds to TTR and prevents dissociation of the TTR tetramer by kinetic stabilization of the native state of the TTR tetramer.

Thus, methods which stabilize TTR in a diseased tissue ameliorate misfolding and lessen symptoms of an associated disease and, depending upon the disease, can contribute to slower progression and/or cure of the disease. The extent of misfolding, and therefore the extent of inhibition achieved by the present methods, can be evaluated by a variety of methods, such as are described in the Examples and in international patent application publication no. WO2004/056315. The disclosure of the above-referenced application is incorporated herein by reference in its entirety.

Thus, methods, which stabilize transthyretin in a tissue, bodily fluid or organ ameliorate misfolding and lessen symptoms of an associated disease and, depending upon the disease, can contribute to slower progression and/or cure of the disease. The target disease of methods of the present disclosure may vary and may include those diseases which result from protein misfolding (e.g., TTR folding) or diseases associated with an increased tendency to form amyloid fibrils of the TTR tetramer found in the bodily fluids such as blood, serum, cerebrospinal fluid, fluids of the central nervous system and eyes. The extent of misfolding, and therefore the extent of inhibition achieved by the present methods, can be evaluated by a variety of methods, such as are described in the Examples.

Accordingly, in another aspect the invention includes a method of treating a TTR amyloid disease, the method comprising administering to a subject diagnosed as having a TTR amyloid disease a therapeutically effective amount of a compound that stabilizes the native state of the TTR tetramer.

In one embodiment, the invention features a method of treating a TTR amyloid disease, the method comprising administering to a subject diagnosed as having a TTR amyloid disease a therapeutically effective amount of a compound disclosed above that stabilizes TTR tetramer.

The TTR amyloid disease can be, for example, familial amyloid polyneuropathy, familial amyloid cardiomyopathy, senile systemic amyloidosis, central amyloidosis or ocular amyloidosis.

The subject treated in the present methods can be a human subject, although it is to be understood that the principles of the invention indicate that the invention is effective with respect to all mammals.

Evaluation of the Activity of the Compounds

A number of in vitro tests can be used to evaluate the compounds for their ability to stabilize TTR tetramers or prevent formation of fibrils. The tests can include a fibril formation assay, a plasma selectivity assay, determination of the three-dimensional structure of a TTR:compound complex (e.g., by X-ray crystallography), kinetics of TTR tetramer dissociation or fibril formations, and determining the stoichiometry and energetics of TTR: compound interactions, by, for example, centrifugation or calorimetry.

The TTR used in the screening methods can be wild type TTR or a mutant TTR, such as a naturally occurring mutant TTR causally associated with the incidence of a TTR amyloid disease such as familial amyloid polyneuropathy or familial amyloid cardiomyopathy. Example naturally occurring mutant TTRs include, but are not limited to, V122I, V30M, L55P (the mutant nomenclature describes the substitution at a recited amino acid position, relative to the wild type; see, e.g., Saraiva et al. *Hum. Mut.* 17:493-503 (2001)).

Examples

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); Room Temperature, RT, rt, and the like.

Materials and Methods

Reagents and Instruments.

Prealbumin from human plasma (human TTR) was purchased from Sigma. Diflunisal, Thyroxine (T4), and resveratrol were purchased from Fisher. All reactions were carried out under argon atmosphere using dry solvents under anhydrous conditions, unless otherwise noted. The solvents used were ACS grade from Fisher. Reagents were purchased from Aldrich and Acros, and used without further purification. Reactions were monitored by thin-layer chromatography (TLC) carried out on 0.20 mm POLYGRAM® SIL silica gel plates (Art.-Nr. 805 023) with fluorescent indicator UV254 using UV light as a visualizing agent. Normal phase flash column chromatography was carried out using Davisil® silica gel (100-200 mesh, Fisher). Wild type TTR concentration is serum was measured at Stanford Medical School using nephelometric analyzer (28 mg/dL or 5 μM).

Chemical Synthesis

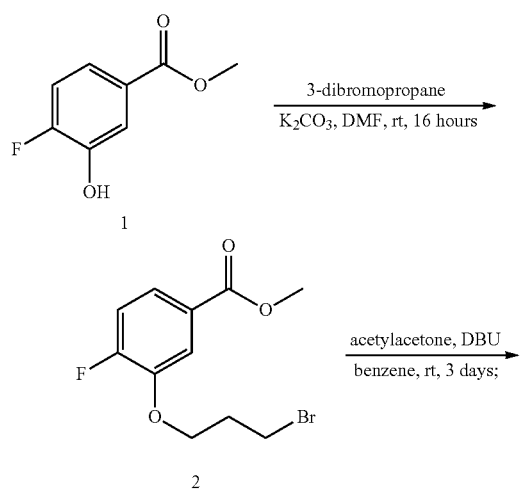

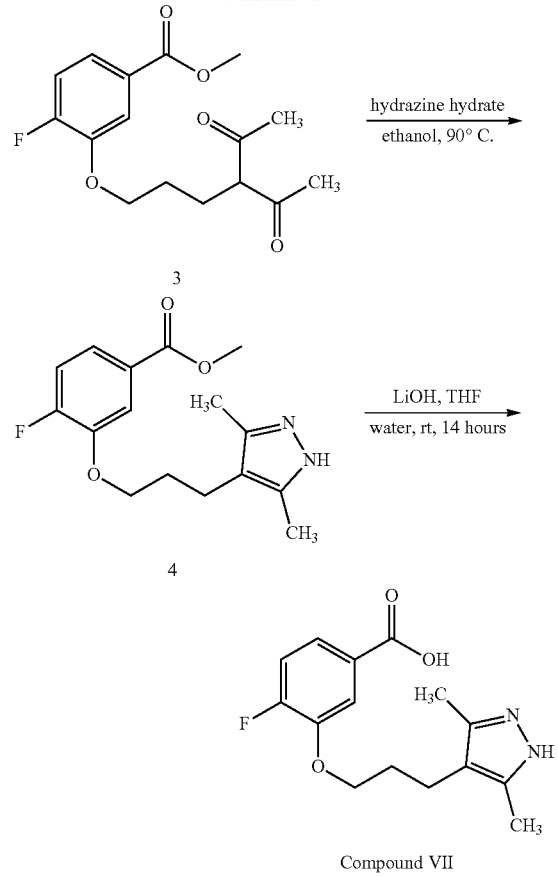

Methyl 3-(3-bromopropoxy)-4-fluorobenzoate (Compound 2)

To a solution of methyl 4-fluoro-3-hydroxybenzoate 1 (3.0 g, 17.6 mmol, 1 equiv) and 1,3-dibromopropane (9.0 ml, 88.2 mmol, 5 equiv) in DMF (40 ml) was added $K_2CO_3$ (2.93 g, 21.2 mmol, 1.2 equiv). The reaction mixture was stirred at room temperature for 16 hours. The mixture was diluted with EtOAc (1.5 L), washed with brine (3×0.5 L) and dried with $Na_2SO_4$. The solution was filtered and concentrated. The residue was purified by flash column chromatography (silica gel, 1-10% EtOAc/hexanes) to afford compound 2 (4.21 g, 82% yield); $^1$H NMR (CD3OD, 600 MHz) δ 7.67-7.61 (m, 2H), 7.14-7.07 (m, 1H), 4.21 (t, 2H, J=5.89 Hz), 3.89 (s, 3H), 3.62 (t, 2H, J=6.38 Hz), 2.38-2.31 (m, 2H); (ESI$^+$) m/z: calcd for $C_{11}H_{12}BrFO_3$+H$^+$290.00; found 290.01 (M+H$^+$).

Methyl 3-(3-(3,5-dimethyl-1H-pyrazol-4-yl) propoxy)-4-fluorobenzoate (Compound 4)

A solution of 2 (780 mg, 2.69 mmol, 1 equiv) in benzene (3 ml) was added dropwise to a solution of acetyl acetone (0.552 ml, 5.38 mmol, 2 equiv) and DBU (0.804 ml, 5.38 mmol, 2 equiv) in benzene (7 ml). The reaction mixture was stirred at room temperature for 3 days. The mixture was filtered and concentrated. The residue was purified by flash column chromatography (silica gel, 1-10% EtOAc/hexanes) to afford compound 3 which was used in the next step directly. Hydrazine hydrate (0.36 ml, 6.73 mmol, 2.5 equiv)

was added to a solution 3 in ethanol (5 ml) and the reaction was heated under reflux for 4 hours. The reaction was concentrated and purified by flash column chromatography (silica gel, 1-20% MeOH/CH$_2$Cl$_2$) to afford compound 4 (288 mg, 35% yield) in two steps; $^1$H NMR (CD$_3$OD, 600 MHz) δ 7.64-7.58 (m, 2H), 7.20-7.15 (m, 1H), 4.01 (t, 2H, J=6.0 Hz), 3.86 (s, 3H), 2.58 (t, 2H, J=7.2 Hz), 2.12 (s, 6H), 1.97-1.92 (m, 2H); HRMS (DART) m/z: calcd for C16H19FN2O+H$^+$307.1458; found 307.1452 (M+H$^+$).

3-(3-(3,5-Dimethyl-1H-pyrazol-4-yl)propoxy)-4-fluorobenzoic acid (Compound VIIc)

To a suspension of 4 (100 mg, 0.33 mmol, 1 equiv) in a mixture of THF (3 ml) and water (3 ml) was added LiOH.H$_2$O (27.5 mg, 0.66 mmol, 2 equiv). The reaction mixture was stirred at room temperature for 14 hr after which it was cooled to 0° C. and carefully acidified to pH 2-3 with 1N aqueous HCl. The mixture was extracted with EtOAc (3×30 ml) and the combined organic extracts were dried over anhydrous sodium sulfate and concentrated in vacuo. The crude product was subjected to flash column chromatography (silica gel, 10-50% MeOH/CH$_2$Cl$_2$) to give Compound VIIc (68 mg, 71% yield) as a white solid (>98% purity by HPLC); $^1$H NMR (CD$_3$OD, 600 MHz) δ 7.65-7.58 (m, 2H), 7.20-7.14 (m, 1H), 4.00 (t, 2H, J=6.0 Hz), 2.58 (t, 2H, J=5.8 Hz), 2.12 (s, 6H), 1.97-1.92 (m, 2H); HRMS (DART) m/z: calcd for C15H17FN2O3+H$^+$293.1301; found 293.1293 (M+H$^+$).

3-(3-(3,5-Dimethyl-1H-pyrazol-4-yl)propoxy)-4-fluorobenzamide

To a suspension of 4 (100 mg, 0.33 mmol, 1 equiv) in a mixture of THF (3 ml) and water (3 ml) is added (23.1 mg, 0.66 mmol, 2 equiv) of NH$_4$OH. The reaction mixture is stirred at room temperature for 14 hr after which it is cooled to 0° C. and carefully adjusted to pH 7 with 1N aqueous HCl. The mixture is extracted with EtOAc (3×30 ml) and the combined organic extracts are dried over anhydrous sodium sulfate and concentrated in vacuo. The crude product is subjected to flash column chromatography (silica gel, 10-50% MeOH/CH$_2$Cl$_2$) to give 3-(3-(3,5-Dimethyl-1H-pyrazol-4-yl)propoxy)-4-fluorobenzamide.

N-ethyl 3-(3-(3,5-Dimethyl-1H-pyrazol-4-yl)propoxy)-4-fluorobenzamide

To a suspension of 4 (100 mg, 0.33 mmol, 1 equiv) in a mixture of THF (3 ml) and water (3 ml) is added (27.1 mg, 0.66 mmol, 2 equiv) of C$_2$H$_5$NH$_2$. The reaction mixture is adjusted to pH 9.0 with 0.5N NaOH, then stirred at room temperature for 14 hr after which it is cooled to 0° C. and carefully adjusted to pH 7 with 1N aqueous HCl. The mixture is extracted with EtOAc (3×30 ml) and the combined organic extracts are dried over anhydrous sodium sulfate and concentrated in vacuo. The crude product is subjected to flash column chromatography (silica gel, 10-50% MeOH/CH$_2$Cl$_2$) to give N-ethyl 3-(3-(3,5-Dimethyl-1H-pyrazol-4-yl)propoxy)-4-fluorobenzamide.

Isothermal Titration Calorimetry (ITC)

Calorimetric titrations were carried out on a VP-ITC calorimeter (MicroCal, Northhampton, Mass.). A solution of test compound (Compound VIIc, Compound A, and Tafamidis) (25 μM in PBS pH 7.4, 100 mM KCl, 1 mM EDTA, 8% DMSO) was prepared and titrated into an ITC cell containing 2 μM of TTR in an identical buffer. Prior to each titration, all samples were degassed for 10 minutes. 37 injections of test compounds (8.0 μL each) were injected into the ITC cell (at 25° C.) to the point that TTR was fully saturated with ligand. Integration of the thermogram after the subtraction of blanks yielded a binding isotherm that fit best to a model of two interacting sites exhibiting negative cooperativity. The data were fit by a nonlinear least squares approach with four adjustable parameters: K$_{d1}$, ΔH1, K$_{d2}$, and ΔH2 using the ITC data analysis module in MicroCal ORIGIN 5.0 software.

Fluorescence Polarization Binding Assays

Determination of FP Probe Displacement by TTR Ligands.

The affinity of test compounds to TTR was determined by their ability to displace FP probe form TTR using our recently developed assay (Alhamadsheh et al. *Science Translational Medicine* (2011)). In a black 384-well plates (E&K Scientific, # EK-31076), FP-probe 5 (200 nM) was incubated with TTR (400 nM) in assay buffer (PBS pH 7.4, 0.01% Triton-X100, 1% DMSO in 25 μL final volumes) at room temperature. Compound VIIc, Compound A, and tafamidis were then added to the wells a single concentration of 10 μM. The samples were allowed to equilibrate by agitation for 30 min at room temperature and fluorescence polarization (excitation λ 485 nm, emission λ 525 nm, cutoff λ 515 nm) measurements were taken using a SpectraMax M5 Microplate Reader (Molecular Devices). The data were fit to the following equation [y=(A−D)/(1+(x/C)^B)+D] where A=maximum FP signal, B=slope, C=apparent binding constant (Kapp), and D=minimum FP signal. The apparent binding constant was reported as the mean for triplicate experiments and the best data fit was determined by R$^2$ value.

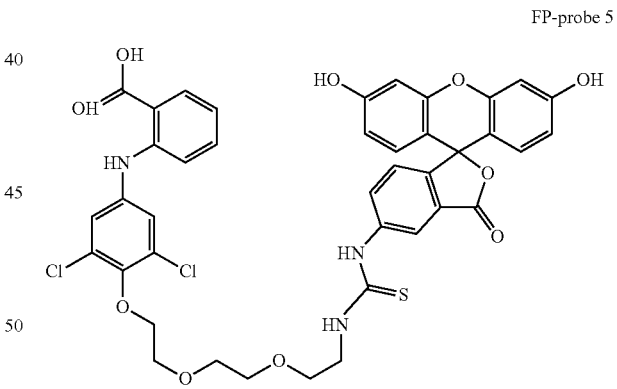

FP-probe 5

Serum TTR Selectivity Assay

The binding affinity and selectivity of the of test compounds to TTR was determined by their ability to compete for covalent probe 6 (shown below) binding to TTR in human serum as previously reported (Choi et al., *Bioorg Med Chem* (2011)). 98 μL of human serum (Sigma-Aldrich) was mixed with 1 μL of test compounds (1.0 mM stock solution in DMSO, final concentration: 10 μM) and 1 μL of covalent probe 6 (0.36 mM stock solution in DMSO: final concentration: 3.6 μM). The fluorescence changes (λ$_{ex}$=328 nm and λ$_{em}$=384 nm) were monitored every 10 min using a microplate spectrophotometer reader (Molecular Devices SpectraMax M5) for 6 h at 25° C.

Covalent probe 6

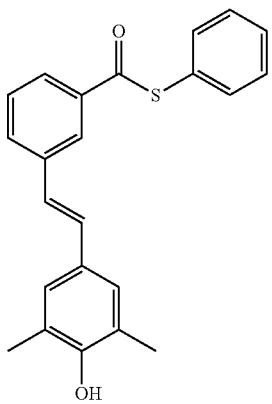

Design and Synthesis of Compound VIIc

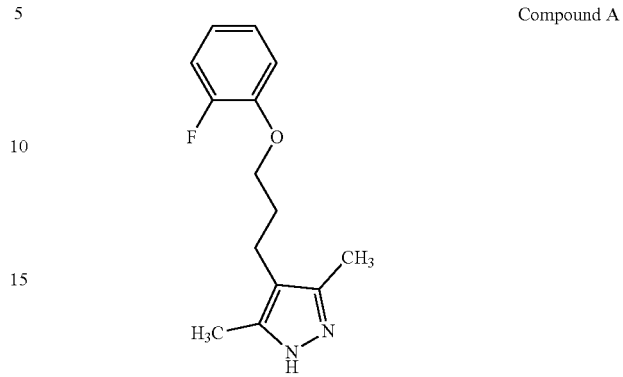

Measurement of Serum WT-TTR Tetramer Stability Against Acid Denaturation

All compounds were 10 mM stock solutions in DMSO and diluted accordingly with DMSO for different assays. 0.5 µl of each compound was added to 24.5 µl of human serum (from human male AB plasma, Sigma) to make the final concentration of 10 µM. The samples were incubated at 37° C. for 2 h, and then 10 µl of the samples were diluted 1:10 with acidification buffer (pH 4.0, 100 mM sodium acetate, 100 mM KCl, 1 mM EDTA, 1 mM DTT). The samples for 0 hours were directly cross-linked with glutaraldehyde (final concentration of 2.5%) for 5 min, and then quenched with 10 µl of 7% sodium borohydride solution in 0.1 M NaOH; while the samples in acidification buffer were incubated at room temperature for 72 h and then cross-linked and quenched with the same protocol. All the samples were denatured with adding 100 µl SDS gel loading buffer and boiled for 5 min. 12.5 µl of each sample was separated in 12% SDS-PAGE gels and analyzed by immunoblotting using anti-TTR antiserum (DAKO A0002). The normalization was done by dividing each value of the TTR tetramer band intensity by the average of all the values at time 0.

Measurement of Serum V122I-TTR Tetramer Stability Against Acid Denaturation

Subjects: Samples were obtained from two patients with the V122I TTR mutation. (mutation confirmed by sequencing/test: 'Amyloidosis DNA titer'): The western blot analysis was performed as described above for wild type TTR. All the value of the TTR tetramer band intensity was normalized by the DMSO treated sample at time 0 which was set as 1.

Cytotoxicity Assay $5 \times 10^3$ cells were seeded on 80 µl growth media (except $2.5 \times 10^4$ Jurkat cells) in each well in 96-well plates and incubate O/N at 37° C. 20 µl of fresh growth media containing each compound were added into each well to make the final concentration ranging from 1-100 µM. DMSO was used for normalization. Cell titer was tested every 24 h using CellTiter 96 non-radioactive cell proliferation assay kit (Promega, Madison, Wis.) at 560 nm absorbance.

Previously we reported the first high-throughput screen (HTS) for TTR ligands, which enabled us to identify a variety of potent and structurally diverse TTR kinetic stabilizers such as Compound A (Alhamadsheh et al. *Science Translational Medicine*, 2011). The 2-fluorophenyl ring of Compound A occupied the outer binding cavity, placing a portion of the aryl ring into the halogen binding pocket (HBP) 1 or 1'. With this observation and additional SAR data obtained from other ligands, we predicted that introducing a carboxylic acid to the 2-fluorophenyl ring of Compound A would allow the molecule to make additional electrostatic interactions with K15 and 15' at the periphery of the pocket. We hypothesized that the formation of both hydrogen bonds and electrostatic interactions with TTR within the $T_4$ binding site would result in higher binding affinity and better TTR stabilization. A series of analogues of Compound A, including Compound VIIc were synthesized that probed the optimal position of the carboxylic acid moiety at the 2-fluorophenyl ring. In comparison to the clinical candidate tafamidis, we find that Compound VIIc is a highly effective and selective stabilizer of both WT and V122I mutant TTR. Compound VIIc also prevents the dissociation of V122I-TTR in serum obtained from FAC patients very effectively. Compound VIIc was not toxic on a number of cell lines, compared to Compound A, which displayed toxicity to certain cell lines at higher concentration (>25 µM). Therefore, by incorporating the carboxylic acid group we developed Compound VIIc, which is more potent and less toxic than the HTS, Compound A. Compound VIIc has surprising properties in comparison to compound A. Biochemical and biophysical assays revealed important insights into the mechanism of how Compound VIIc is able to bind V122I-TTR with high selectivity and to stabilize the TTR tetramer.

Characterization of Compound VIIc Binding Energetics to TTR

Figure 1:
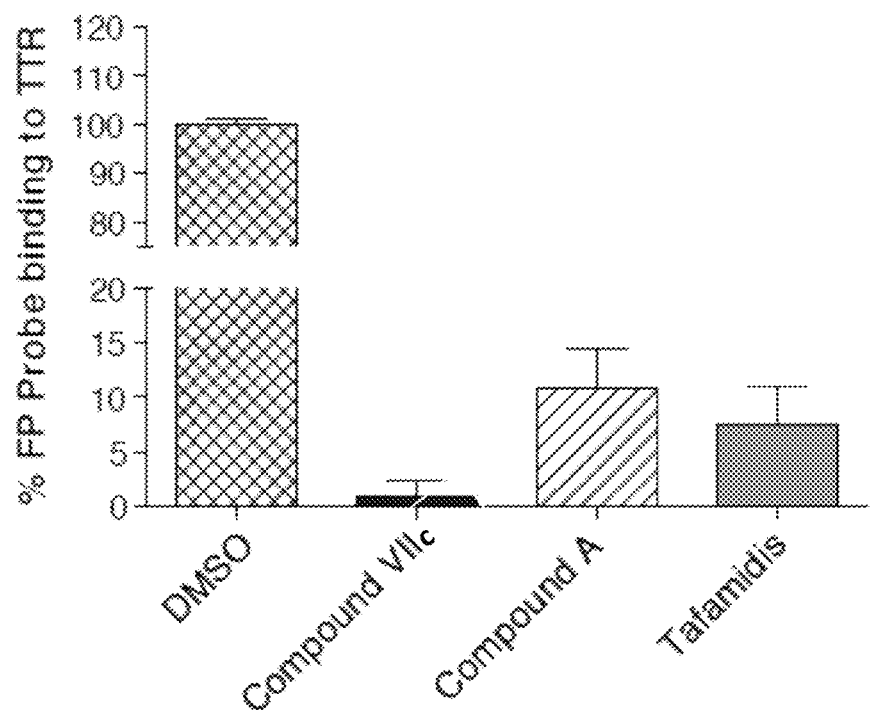
FIG. 1 illustrates the evaluation of ligands binding (Compound VIIc, Compound A, and tafamidis) to TTR in buffer by fluorescence polarization.
Figure 2:
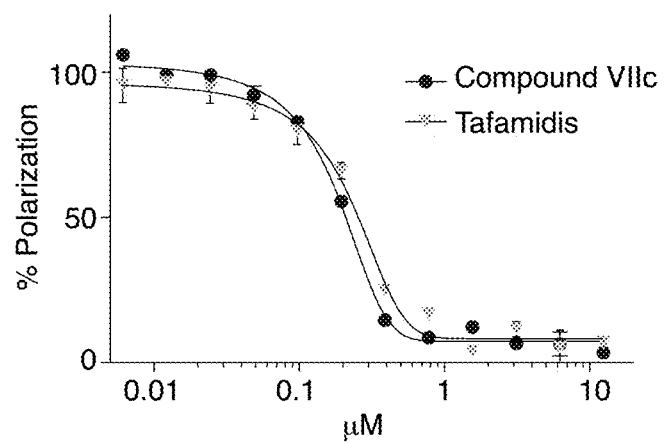
FIG. 2 depicts the competition of FP-probe 5 from TTR by increasing concentrations (0.003 to 100 μM) of Compound VIIc ($K_{app}$=193 nM, $R^2$=0.994) and tafamidis ($K_{app}$=247 nM, $R^2$=0.990). Each point shows the mean +/− SD of three replicates.
Figure 3:
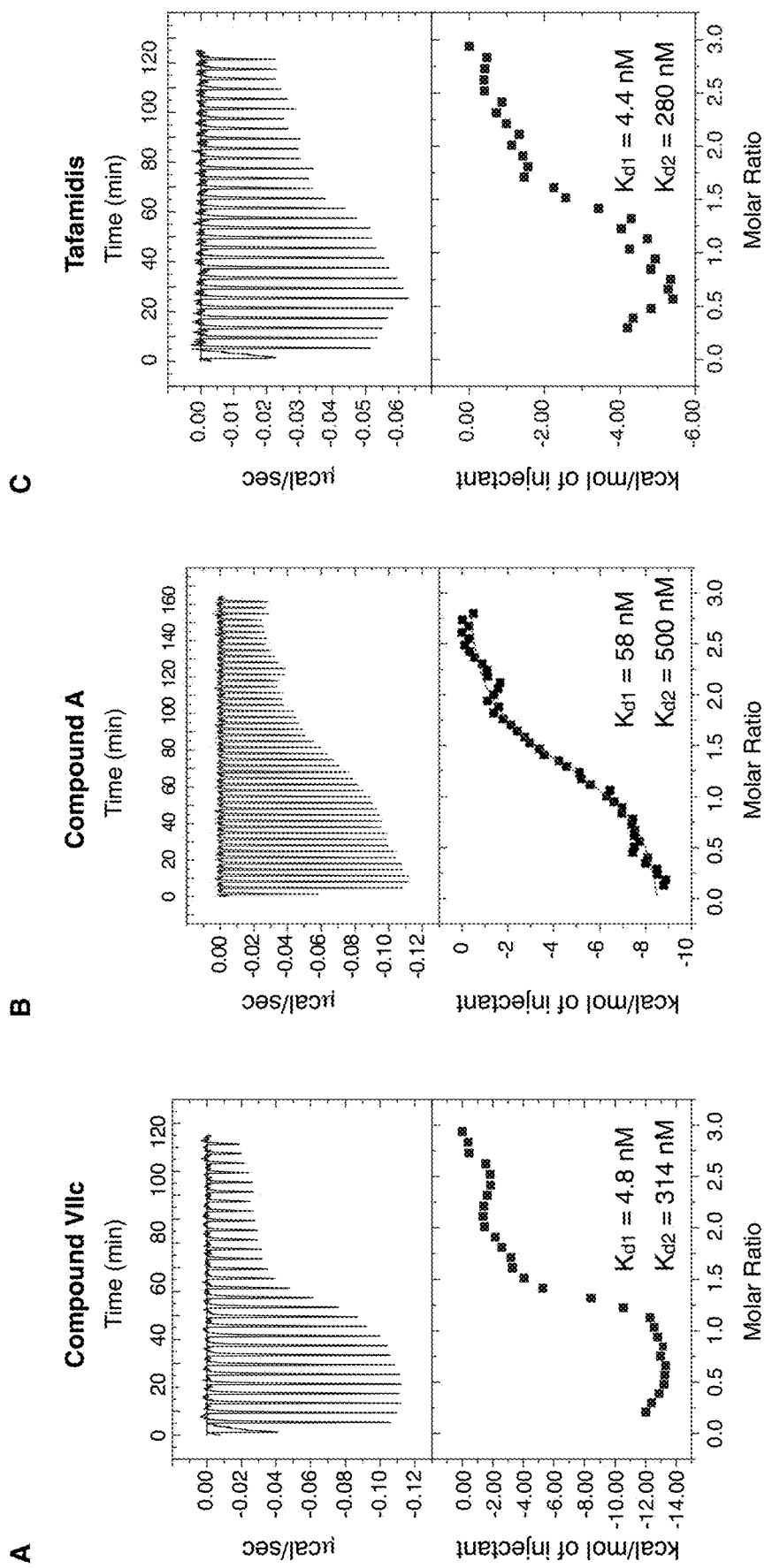
FIG. 3 depicts the assessment of the binding affinity of Compound VIIc, Compound A, and tafamidis to TTR by isothermal titration calorimetry. (A) Calorimetric titration of Compound VIIc against TTR ($K_{d1}$=4.8 nM and $K_{d2}$=314 nM). (B) Calorimetric titration of Compound A against TTR ($K_{d1}$=58 nM and $K_{d2}$=500 nM). (C) Calorimetric titration of tafamidis against TTR ($K_{d1}$=4.4 nM and $K_{d2}$=280 nM). Raw data (top) and integrated heats (bottom) from the titration of TTR (2 μM) with test compounds (25 μM).

The binding affinity of Compound VIIc to TTR at physiological pH was determined using our established fluorescence polarization (FP) assay (FIGS. 1 and 2). For comparison, we also tested four known potent TTR kinetic stabilizers (tafamidis and diflunisal are in clinical trials for TTR amyloidosis; $T_4$ is a natural ligand for TTR; and resveratrol, a natural product that has been shown to prevent TTR aggregation in vitro and TTR-induced cytotoxicity in tissue culture) (FIG. 1). The FP assay is a competitive assay that allows measurement of ligands binding to TTR based on their ability to displace a fluorescent probe from the TTR $T_4$-binding sites (FP-probe 5, above). All test compounds were able to bind to TTR (purified from human plasma) at 10 μM (FIG. 4). The top two compounds, Compound VIIc and tafamidis, were then assayed in a multi-point dose-response FP assay (concentration range between 0.003 and 100 μM). The apparent binding constant of Compound VIIc ($K_{app}$=193 nM, $R^2$=0.994) was similar to that of tafamidis ($K_{app}$=247 nM, $R^2$=0.990) (FIG. 2). Many ligands, including tafamidis ($K_{d1}$=4.4 nM and $K_{d2}$=280 nM) (FIG. 3C), bind TTR with negative cooperativity. We used isothermal titration calorimetry (ITC) to determine the binding constants of Compound VIIc to TTR and also to evaluate cooperativity between the two TTR $T_4$ sites. ITC measurements showed that the $K_{d1}$ of compound VIIc ($K_{d1}$=4.8 nM) was an order of magnitude lower than the $K_{d1}$ of compound A ($K_{d1}$=58 nM), indicating a higher affinity of compound VIIc for TTR. Analysis of the free energies associated with Compound VIIc binding to TTR shows high binding affinity and the dissociation constants indicate that Compound VIIc binds TTR with negative cooperativity ($K_{d1}$=4.8 nM and $K_{d2}$=314 nM) (FIG. 3A). Despite the similar binding affinities of Compound VIIc and tafamidis (i.e. similar ΔG values; $\Delta G_1$~−11.4 and $\Delta G_2$~−8.8), the binding nature of both compounds to TTR is very different. While Compound VIIc binding is almost entirely enthalpically driven (ΔH1=−13.6 kcal/mol and ΔH2=−7.5 kcal/mol), tafamidis binding is about 50% entropy and 50% enthalpy (ΔH1=−5.0 kcal/mol and ΔH2=−3.9 kcal/mol).

Compound VIIc Binds with High Selectivity to WT-TTR in Human Serum

To stabilize the TTR tetramer and thus prevent amyloid formation and development of cardiac infiltrates in FAC and SSA patients, small molecules must be able to selectively bind to TTR in the presence of more than 4,000 other human serum proteins. We examined the binding selectivity of Compound VIIc to TTR in human serum by a fluorescent conjugate competition assay using a covalent probe 6. Covalent probe 6 binds selectively to TTR in serum and covalently modifies K15, creating a fluorescent conjugate. Ligands that bind with high selectivity to TTR in serum decrease covalent probe 6 binding to TTR and therefore lower the fluorescence. All test compounds (10 μM) were incubated with human serum (WT-TTR concentration ~5 μM) in the presence of covalent probe 6 (3.6 μM) (FIG. 4). Interestingly, Compound VIIc, which binds with high affinity to TTR in buffer was, when compared to tafamidis and Compound A (70.5±1.4% and 59.3±8.7% probe binding, respectively), the most selective TTR ligand in serum (3.1±2.9% probe binding) (FIG. 4B).

Our experiments show that both the selectivity as well as the efficacy of TTR kinetic stabilizers can be greatly increased when the ligand orientation within the $T_4$ pocket is optimized. This is evidenced by Compound VIIc outperforming Compound A and tafamidis in stabilizing TTR at stoichiometric concentrations in human serum. Interestingly, despite the similar binding affinities of Compound VIIc and tafamidis to TTR in buffer, their selectivity for TTR in serum is different. Binding to serum proteins is an important factor in determining the overall selectivity, toxicity and pharmacokinetics of a drug. In comparison to tafamidis and Compound A, Compound VIIc exhibited remarkable selectivity for binding TTR in human serum in the presence of more than 4,000 other human serum proteins such as albumin (FIGS. 4-6). The exceptional binding selectivity of Compound VIIc to serum TTR surpasses that of TTR's natural ligand, $T_4$ as well as that of tafamidis and Compound A.

Compound VIIc Increases the Stability of Both WT-TTR and V122I-TTR in Human Serum Against Acid-Mediated Dissociation and Amyloidogenesis The compounds were tested for their ability to stabilize WT-TTR in human serum (FIG. 5). TTR tetramer dissociation to monomers and subsequent aggregation occur very inefficiently at neutral pH. To measure the stabilizing effect of Compound VIIc, Compound A, and tafamidis towards TTR we used an acid-mediated tetramer dissociation assay. Test compounds (10 μM) were pre-incubated with human serum (TTR ~5 μM) and the pH was lowered to pH 4.0 to induce aggregation. Aliquots, taken at 0 and 72 hours, were treated with glutaraldehyde to cross-link TTR tetramers that remained intact in the serum sample. SDS-PAGE followed by immunoblot analysis was used to measure the amount of intact TTR tetramer after 72 hours of acid treatment in the presence and absence of test compounds. In clinical trials of tafamidis the mean maximum concentration ($C_{max}$) of tafamidis in the serum of human subjects, following 20 mg daily dose, was estimated to be around 7.4 μM (Tafamidis Meglumine (Vyndaqel) assessment report, European Medicines Agency (EMA) (2011) Procedure No.: EMEA/H/C/002294). At 10 μM, tafamidis stabilized about 58%+/−3% of the TTR tetramer in serum. Compound A provided similar stabilizing effect to that of tafamidis (61.7%+/−2.1% TTR tetramer stabilization at 10 μM). In contrast, at 10 μM, Compound VIIc was very effective and stabilized the majority (108+/−6%) of serum WT-TTR. The dramatically increased stabilizing effect of Compound VIIc compared to Compound A and Tafamidis was unanticipated and surprising. At 10 μM, Compound VIIc was also very effective in stabilizing almost all the V122I-TTR mutant in serum samples form FAC patients (~100%) (FIG. 6). Due to its ability to stabilize WT- and V122I-TTR, we anticipate Compound VIIc to be effective against both SSA and FAC.

Compound VIIc Shows No Cytotoxicity In Vitro

In vitro cytotoxicity assays showed that has no in vitro cytotoxicity towards a panel of cell lines (FIG. 7).

The effect of both Compound VIIc and tafamidis on the viability and proliferation of four cell lines was studied via the (3-(4,5-dimethylthiazol-2-yl)-2,5-diphenyltetrazolium bromide (MTT) assay (FIG. 7). Compounds were added to the culture medium at different concentrations (concentration range from 1 to 100 μM) and the cells were incubated for additional 24 h at 37° C. Compound VIIc showed no cytotoxic effects towards any of the cell lines that were tested, while Compound A shows cytotoxicity at high concentrations (>25 μM) towards Hep3B and Hela cells (FIG. 7). These data indicate that the Compound VIIc has less cytotoxicity than Compound A and suggest a better safety profile of Compound VIIc. Cytotoxicity results tafamidis were similar to Compound VIIc, except towards MCF7 cells, where cytotoxic effects were observed at higher concentrations (>50 μM).

Heterobifunctional Compounds for PPI Disruption

Selection of the Linker.

The linker is selected considering the biophysical properties of the interacting proteins (Rp: recruited protein, and Tp: target protein). Given the bifunctional compound effectively acts to form a protein complex, the long-range forces that govern protein-protein interaction are considered when selecting an appropriate linker. The effect of the electrostatic interaction may be favorable, unfavourable or small. If the effect is small, the linker is selected to merely be long enough to project the targeting moiety (T) out of the binding pocket. If the interaction between Rp (recruited protein) and Tp (target protein) is disfavoured the linker is selected to be longer. The longer the linker (e.g., a flexible linker), the greater the area explored by the targeting element. Although this allows the targeting element to bind to the protein Tp, the effective concentration of the T decreases as the area explored increases. The flexibility of the linker also introduces an entropic cost for small flexible linkers, due to the restriction of conformational states in the final bifunctional complex. As the linker increases in length this penalty is reduced. Introduction of rigid elements into the linker restricts the conformational space explored by T, and provided it is sufficiently long allows it to project from the protein, with a reduced conformational penalty. Using a series of linker systems, a library of bifunctional molecules is prepared for a wide variety of interacting proteins.

Linkers of various length, hydrophilicity, and rigidity are used in the preparation of bifunctional compounds. The linkers are attached to activated functional groups on the small molecule targeting and recruitment moieties using any convenient organic coupling reactions (e.g., ester, amide, and ether bond formation reactions).

Selection of Targeting Moieties.

Any small molecule ligand of a target protein or target protein/receptor pair can be used. In addition, targeting moieties are identified by small molecule microarrays (SMM) screening for binding to the target protein using computational approaches. The attachment site for the linker on the TTR ligand is determined by the co-crystal structure of the ligand bound to TTR.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of stabilizing transthyretin (TTR) in a tissue or biological fluid, the method comprising contacting the tissue or biological fluid with Compound VIIa:

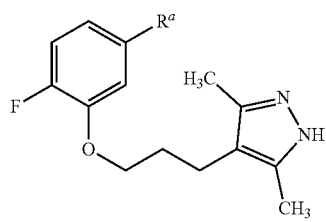

(VIIa)

where $R^a$ is selected from the group consisting of OH, CHO, COOH, $CONH_2$, CONH(OH), $COOR^6$, and $CONHR^6$; and $R^6$ is straight or branched alkyl of 1-3 carbon atoms;

or a pharmaceutically acceptable salt thereof.

2. The method of claim 1, wherein $R^a$ is selected from the group consisting of COOH $CONH_2$, CONH(OH), $COOR^6$, and $CONHR^6$.

3. The method of claim 1, wherein Compound VIIa has a structure of Compound VIIc

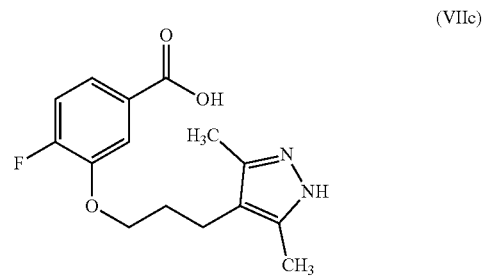

(VIIc)

or a pharmaceutically acceptable salt thereof.

4. A method of decreasing amyloid fibril formation in a tissue or biological fluid, the method comprising contacting the tissue or biological fluid with Compound VIIa:

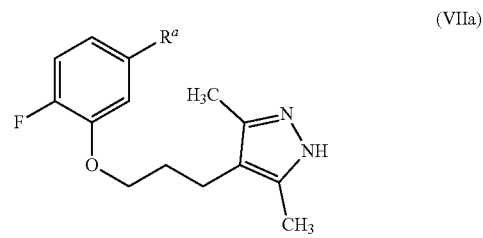

(VIIa)

where $R^a$ is selected from the group consisting of OH, CHO, COOH, $CONH_2$, CONH(OH), $COOR^6$, and $CONHR^6$; and $R^6$ is straight or branched alkyl of 1-3 carbon atoms;

or a pharmaceutically acceptable salt thereof.

5. The method of claim 4, wherein $R^a$ is selected from the group consisting of COOH $CONH_2$, CONH(OH), $COOR^6$, and $CONHR^6$.

6. The method of claim 4, wherein Compound VIIa has a structure of Compound VIIc

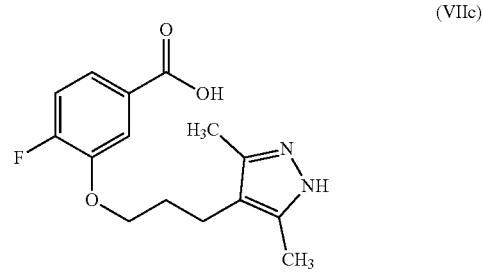 [SMILES: Cc1n[nH]c(C)c1CCCOc1cc(C(=O)O)ccc1F]

(VIIc)

or a pharmaceutically acceptable salt thereof.

7. A method of determining the presence and/or concentration of transthyretin (TTR) in a sample comprising biological fluid or tissue, comprising:
a) adding a labeled Compound VIIa to the sample

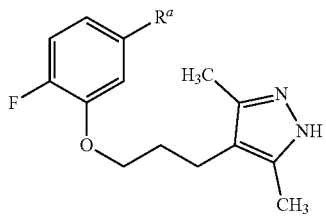

(VIIa)

where $R^a$ is selected from the group consisting of OH, CHO, COOH, $CONH_2$, CONH(OH), $COOR^6$, and $CONHR^6$; and
$R^6$ is straight or branched alkyl of 1-3 carbon atoms;
or a pharmaceutically acceptable salt thereof;
b) allowing binding of the labeled compound to TTR; and
c) measuring distance-dependent energy transfer between the labeled Compound VIIa bound to a $T_4$ binding pocket and a labeled compound and/or peptide and/or protein bound to an orthogonal binding surface on the TTR tetramer.

8. The method of claim 7, wherein $R^a$ is selected from the group consisting of COOH $CONH_2$, CONH(OH), $COOR^6$, and $CONHR^6$.

9. The method of claim 7, wherein Compound VIIa has a structure of Compound VIIc

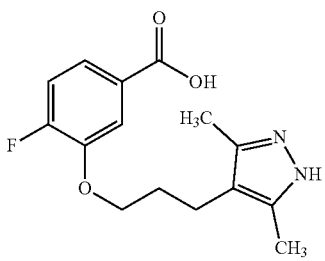

(VIIc)

or a pharmaceutically acceptable salt thereof.

* * * * *

Disclaimer

10,842,777 B2 - Isabella A. Graef, Woodside; Mamoun M. Alhamadsheh, Fremont, both of CA (US). COMPOUNDS AND COMPOSITIONS THAT BIND AND STABILIZE TRANSTHYRETIN AND THEIR USE FOR INHIBITING TRANSTHYRETIN AMYLOIDOSIS AND PROTEIN-PROTEIN INTERACTIONS. Patent dated November 24, 2020. Disclaimer filed January 13, 2025, by the assignee, The Board of Trustees of the Leland Stanford Junior University.

The term of this patent shall not extend beyond the expiration date of Patent Nos. 9,642,838; 10,398,681; 8,877,795; 9,308,209; 10,039,726; 10,278,929 and 11,337,935.

*(Official Gazette, April 22, 2025)*